(12) United States Patent
Mohapatra et al.

(10) Patent No.: US 9,089,589 B2
(45) Date of Patent: Jul. 28, 2015

(54) MICRO-RNAS MODULATING IMMUNITY AND INFLAMMATION

(71) Applicant: UNIVERSITY OF SOUTH FLORIDA, Tampa, FL (US)

(72) Inventors: Shyam S. Mohapatra, Lutz, FL (US); Jia-Wang Wang, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 13/772,035

(22) Filed: Feb. 20, 2013

(65) Prior Publication Data

US 2013/0216605 A1  Aug. 22, 2013

Related U.S. Application Data

(62) Division of application No. 12/600,803, filed as application No. PCT/US2008/064678 on May 23, 2008, now Pat. No. 8,415,096.

(60) Provisional application No. 60/939,902, filed on May 24, 2007, provisional application No. 60/939,769, filed on May 23, 2007.

(51) Int. Cl.
   *A61K 31/7105* (2006.01)
   *C12Q 1/68* (2006.01)

(52) U.S. Cl.
   CPC .......... *A61K 31/7105* (2013.01); *C12Q 1/6809* (2013.01); *C12Q 1/6883* (2013.01); *C12Q 2600/136* (2013.01); *C12Q 2600/178* (2013.01)

(58) Field of Classification Search
   USPC .................. 435/6, 91.1, 91.31, 455; 514/44; 536/23.1, 24.3, 24.5
   See application file for complete search history.

(56) References Cited

U.S. PATENT DOCUMENTS

| | | | |
|---|---|---|---|
| 6,489,306 B2 | 12/2002 | Mohapatra et al. | |
| 6,900,299 B1 | 5/2005 | Mohapatra et al. | |
| 7,118,888 B2 | 10/2006 | Mohapatra et al. | |
| 7,354,908 B2 | 4/2008 | Mohapatra et al. | |
| 7,371,738 B2 | 5/2008 | Mohapatra et al. | |
| 7,595,303 B1 | 9/2009 | Mohapatra et al. | |
| 7,655,772 B2 | 2/2010 | Mohapatra | |
| 7,892,553 B2 | 2/2011 | Mohapatra et al. | |
| 8,071,560 B2 | 12/2011 | Mohapatra et al. | |
| 8,148,114 B2 | 4/2012 | Mohapatra et al. | |
| 2003/0198624 A1 | 10/2003 | Mohapatra et al. | |
| 2004/0005615 A1 | 1/2004 | Li et al. | |
| 2005/0159385 A1 | 7/2005 | Mohapatra | |
| 2005/0191272 A1 | 9/2005 | Hakonarson et al. | |
| 2005/0266093 A1 | 12/2005 | Mohapatra | |
| 2006/0015263 A1 | 1/2006 | Stupp et al. | |
| 2006/0019286 A1 | 1/2006 | Horvitz et al. | |
| 2006/0239971 A1 | 10/2006 | Mohapatra | |
| 2007/0036867 A1 | 2/2007 | Mohapatra et al. | |
| 2007/0238676 A1 | 10/2007 | Mohapatra et al. | |
| 2008/0023325 A1 | 1/2008 | Mohapatra et al. | |
| 2008/0070858 A1 | 3/2008 | Mohapatra | |
| 2008/0076674 A1 | 3/2008 | Litman et al. | |
| 2008/0214437 A1 | 9/2008 | Mohapatra et al. | |
| 2009/0004668 A1* | 1/2009 | Chen et al. ..................... 435/6 |
| 2009/0137504 A1 | 5/2009 | Echwald et al. | |
| 2009/0226423 A1 | 9/2009 | Mohapatra et al. | |
| 2009/0280143 A1 | 11/2009 | Mohapatra et al. | |
| 2010/0009367 A1 | 1/2010 | Sommer et al. | |
| 2010/0010073 A1 | 1/2010 | Thum et al. | |
| 2010/0184046 A1 | 7/2010 | Klass et al. | |
| 2010/0286249 A1 | 11/2010 | Mohapatra et al. | |
| 2011/0052558 A1 | 3/2011 | Mohapatra et al. | |
| 2011/0052601 A1 | 3/2011 | Mohapatra et al. | |
| 2011/0190372 A1 | 8/2011 | Tomic-Canic et al. | |
| 2011/0313025 A1 | 12/2011 | Brown et al. | |
| 2012/0093781 A1 | 4/2012 | Mohapatra et al. | |
| 2012/0122216 A1 | 5/2012 | Esau et al. | |
| 2012/0165392 A1 | 6/2012 | Olson et al. | |
| 2012/0289420 A1 | 11/2012 | Mohapatra et al. | |
| 2013/0274140 A1* | 10/2013 | Croce et al. ..................... 506/9 |

FOREIGN PATENT DOCUMENTS

| | | |
|---|---|---|
| WO | WO 03/028759 | 4/2003 |
| WO | WO 03/074561 | 9/2003 |
| WO | WO 03/092618 | 11/2003 |
| WO | WO 2004/022003 | 3/2004 |
| WO | WO 2004/074314 | 9/2004 |
| WO | WO 2004/076664 | 9/2004 |
| WO | WO 2005/056021 | 6/2005 |
| WO | WO 2005/094420 | 10/2005 |
| WO | WO 2005/105136 | 11/2005 |

(Continued)

OTHER PUBLICATIONS

Doench et al., Genes and Development, vol. 18, No. 5, pp. 504-511 (2004).*
Holen et al., Nucleic Acids Res., vol. 30, No. 8, pp. 1757-1766 (2002).*
Opalinska et al., Nature Rev., vol. 1, pp. 503-514 (2002).*
Perrachi et al., Rev. Med. Virol., vol. 14, pp. 47-64 (2004).*
Crooke, S., Ann. Rev. Medicine, vol. 55, pp. 61-95 (2004).*
Agrawal et al., Molecular Med. Today, vol. 6, pp. 72-81 (2000).*
Chirila et al., Biomaterials, vol. 23, pp. 321-342 (2002).*

(Continued)

*Primary Examiner* — Jane Zara

(74) *Attorney, Agent, or Firm* — Saliwanchik, Lloyd & Eisenschenk

(57) ABSTRACT

MicroRNAs are shown to be up- and/or down-regulated in inflammation and immune cells using a mouse model of asthma and regulatory T cells as source of RNA, respectively. Modulating the expression of these microRNAs can be effective in redirecting inflammation and immunity and hence, can be beneficial as biomarkers or as therapeutic agents against diverse human immunologic and inflammatory diseases.

10 Claims, 23 Drawing Sheets

(56) References Cited

FOREIGN PATENT DOCUMENTS

| WO | WO 2007/035684 | | 3/2007 |
|---|---|---|---|
| WO | WO 2007/127487 | | 11/2007 |
| WO | WO 2008/036765 | | 3/2008 |
| WO | WO 2008/073915 | | 6/2008 |
| WO | WO 2008/079303 | * | 7/2008 |
| WO | WO 2008/116267 | | 10/2008 |
| WO | WO 2009/036332 | | 3/2009 |
| WO | WO 2009/073527 | | 6/2009 |
| WO | WO 2009/132273 | | 10/2009 |
| WO | WO 2010/105215 | | 9/2010 |
| WO | WO 2010/135570 | | 11/2010 |
| WO | WO 2010/135692 | | 11/2010 |
| WO | WO 2010/139811 | | 12/2010 |
| WO | WO 2011/103502 | | 8/2011 |

OTHER PUBLICATIONS

Jang et al, Expert Rev. Medical Devices, vol. 1, No. 1, pp. 390-394 (2004).*
Paroo et al., Treands in Biotech, vol. 22, No. 8, pp. 390-394 (2004).*
Arial D et al., "The role and regulation of microRNAs in asthma" *Current Opinion Allergy and Clinical Immunology*, 2012, 12(1):49-52.
Bowman RV et al., "Epigenomic targets for the treatment of respiratory diseases" *Expert Opinion on Therapeutic Targets*, 2009, 13(6):625-640.
Chiba Y et al., "Down-Regulation of miR-133a Contributes to Up-Regulation of RhoA in Bronchial Smooth Muscle Cells" *American Journal of Respiratory and Critical Care Medicine*, 2009, 180:713-719.
Chiba Y et al., "MicroRNAs and Their Therapeutic Potential for Human Diseases: MiR-133a and Bronchial Smooth Muscles Hyperresponsiveness in Asthma" *Journal of Pharmacological Sciences*, 2010, 114:164-168.
Collison A et al., "Altered expression of microRNA in the airway wall in chronic asthma: miR-126 as a potential therapeutic target" *BMC Pulmonary Medicine*, 2011, 11:29-34.
Collison A et al., "Inhibition of house dust mite-induced allergic airways disease by antagonism of microRNA-145 is comparable to glucocorticoid treatment" *Journal of Allergy and Clinical Immunology*, 2011, 128:160-167.
Dalal SR et al., "The Role of MicroRNA in Inflammatory Bowel Disease" *Gastroenterology & Hepatology*, 2010, 6(11):714-722.
Drexler SK et al., "The role of Toll-like receptors in chronic inflammation" *The International Journal of Biochemistry & Cell Biology*, 2010, 42:506-518.
Durham AL et al., "Epigenetics of asthma" *Biochimica et Biophysica Acta*, 2011, 1810:1103-1109.
Garbacki N et al., "Matrix metalloproteinase 12 silencing: A therapeutic approach to treat pathological lung tissue remodeling?" *Pulmonary Pharmacology & Therapeutics*, 2009, 22:267-278.
Garbacki N et al., "MicroRNAs Profiling in Murine Models of Acute and Chronic Asthma: A Relationship with mRNAs Targets" *PLoS ONE*, 2011, 6(1):e16509.
Giangreco A et al., "Lung Cancer and Lung Stem Cells Strange Bedfellows?"*American Journal of Respiratory and Critical Care Medicine*, 2007, 175:547-553.
Goncharova EA et al., "Interferons modulate mitogen-induced protein synthesis in airway smooth muscle" *American Journal of Physiology. Lung Cellular and Molecular Physiology*, 2010, 299:L25-L35.
Gower AC et al., "Transcriptomic Studies of the Airway Field of Injury Associated with Smoking-Related Lung Disease" *Proc Am Thor Soc*, 2011, 8:173-179.
Ho SM et al., "Environmental epigenetics of asthma: An update" *Journal of Allergy and Clinical Immunology.*, 2010, 126(3):453-465.
Jiang X, "The emerging role of microRNAs in asthma" *Molecular and Cellular Biochemistry*, 2011, 353:35-40.

Koppelman GH et al., "Recent advances in the epigenetics and genomics of asthma" *Current Opinion Allergy and Clinical Immunology*, 2011, 11:414-419.
Kumar M et al., "Let-7 microRNA-mediated regulation of IL-13 and allergic airway inflammation" *Journal of Allergy and Clinical Immunology*, 2011, 128(5):1077-1085.e10.
Kumar M et al., "Proinflammatory Role of *let-7* miRNAs in Experimental Asthma?" *The Journal of Biological Chemistry*, 2010, 285(48):le19.
Kumar RK et al., "Epigenetic changes in childhood asthma" *Disease Models & Mechanisms*, 2009, 2:549-553.
Lin KW et al., "Emerging pathways in asthma: Innate and adaptive interactions" *Biochimica et Biophysica Acta*, 2011, 1810:1052-1058.
Lu TX et al., "MicroRNA-21 Is Up-Regulated in Allergic Airway Inflammation and Regulates IL-12p35 Expression" *Journal of Immunology*, 2009, 182:4994-5002.
Lu TX et al., "MicroRNA-21 Limits In Vivo Immune Response-Mediated Activation of the IL-12/IFN-γ Pathway, Th1 Polarization, and the Severity of Delayed-Type Hypersensitivity" *Journal of Immunology*, 2011, 187:3362-3373.
Maes T et al., "Gene Therapy for Allergic Airway Diseases" *Current Allergy and Asthma Reports*, 2011, 11:163-172.
Martinez-Nunez RT et al., "The Interleukin 13 (IL-13) Pathways in Human Macrophages Is Modulated by MicroRNA-155 via Direct Targeting of Interleukin 13 Receptor α1 (IL13Rα1)" *The Journal of Biological Chemistry*, 2011, 286(3):14786-1794.
Mattes J et al., "Regulation of MicroRNA by Antagomirs" *American Journal of Respiratory Cell and Molecular Biology*, 2007, 36:8-12.
Mattes J et al., "Emerging role of microRNAs in disease pathogenesis and strategies for therapeutic modulation" *Current Opinion in Molecular Therapeutics*, 2008, 10(2):150-157.
Mattes J et al., "Antagonism of microRNA-126 suppresses the effector function of $T_H2$ cells and the development of allergic airways disease" *PNAS*, 2009, 106(44):18704-18709.
Mayoral RJ et al., "MiR-221 Influences Effector Functions and Actin Cytoskeleton in Mast Cells" *PLoS One*, 2011, 6(10):E26133.
McKiernan PJ et al., "SLPI and inflammatory lung disease in females" *Biochemical Society Transactions*, 2011, 39(5):1421-1426.
Miller RL et al., "Environmental Epigenetics and Asthma" *American Journal of Respiratory and Critical Care Medicine*, 2008, 177:567-573.
Moffatt MF et al., "Genes in asthma: new genes and new ways" *Current Opinion Allergy and Clinical Immunology*, 2008, 8:411-417.
Mohamed JS et al., "Mechanical Stretch Up-regulates MicroRNA-26a and Induces Human Airway Smooth Muscle Hypertrophy by Suppressing Glycogen Synthase Kinase-3β" *The Journal of Biological Chemistry*, 2010, 285(38):29336-29347.
Moschos SA et al., "Expression profiling in vivo demonstrates rapid changes in lung microRNA levels following lipopolysaccharide-induced inflammation but not in the anti-inflammatory action of glucocorticoids" *BMC Genomics*, 2007, 8:240.
Oglesby IK et al., "MicroRNAs in inflammatory lung disease—master regulators or target practice?" *Respiratory Research*, 2010, 11:148.
Pagdin T et al., "MicroRNAs in lung diseases" *Thorax*, 2012, 67:183-184.
Polikepahad S et al., "Proinflammatory Role for *let-7* MicroRNAS in Experimental Asthma" *The Journal of Biological Chemistry*, 2010, 285(39):30139-30149.
Popescu FD et al., "A review of antisense therapeutic interventions for molecular biological targets in asthma" *Biologics: Targets & Therapy*, 2007, 1(3):271-283.
Radzikinas K et al., "A Shh/miR-206/BDNF Cascade Coordinates Innervation and Formation of Airway Smooth Muscle" *Journal of Neuroscience*, 2011, 31(43):15407-15415.
Scrivo R et al., "Inflammation as "common soil" of the multifactorial diseases" *Autoimmunity Reviews*, 2011, 10:369-374.
Sittka A and Schmeck B, "MicroRNAs in the Lung" *MicroRNA Cancer Regulation: Advances in Experimental Medicine and Biology*, 2013, 7740121-134.
Steiner DF et al., "MicroRNA-29 Regulates T-Box Transcription Factors and Interferon-γ Production in Helper T Cells" *Immunity*, 2011, 35:169-181.

(56) References Cited

OTHER PUBLICATIONS

Su SW et al., "Association Between Single-Nucleotide Polymorphisms in Pre-miRNAs and the Risk of Asthma in a Chinese Population" *DNA and Cell Biology*, 2011, 30(11):919-923.

Tan Z et al., "Allele-Specific Targeting of microRNAs to HLA-G and Risk of Asthma" The American Journal of Human Genetics, 2007, 80:829-834.

Thomas LF et al., "Inferring causative variants in microRNA target sites" *Nucleic Acids Research*, 2011, 39(16):e109.

Thomas MF et al., "Construction of Small RNA cDNA Libraries for Deep Sequencing" *Methods in Molecular Biology*, 2010, 667:93-111.

Tsitsiou E et al., "Transcriptome analysis shows activation of circulating CD8+ T cells in patients with severe asthma" *Journal of Allergy and Clinical Immunology*, 2012, 129(1):95-103.

Vohwinkel CU et al., "Elevated $CO_2$ Levels Cause Mitochondrial Dysfunction and Impair Cell Proliferation" *The Journal of Biological Chemistry*, 2011, 286(43):37067-37076.

Wang JW et al., "Regulating the Regulators: microRNA and Asthma" *WAO Journal*, 2011, 4:94-103.

Williams AE et al., "MicroRNA Expression Profiling in Mild Asthmatic Human Airways and Effect of Corticosteroid Therapy" *PLoS One*, 2009, 4(6):e5889.

Wu W et al., "Chronic lung diseases" *Wiley interdisciplinary reviews*, 2009, 1(3):298-308.

Yang M et al., "Discovery, biology and therapeutic potential of RNA interference, microRNA and antagomirs" *Pharmacology & Therapeutics*, 2008, 117:94-104.

Zhao W et al., "Toward a Systematic Understanding of mRNA 3' Untranslated Regions" *Proceedings of the American Thoracic Society*, 2011, 8:163-166.

Zomer A et al., "Exosomes Fit to deliver small RNA" *Communicative & Integrative Biology*, 2010, 3(5):447-450.

Chen, X et al., "Characterization of microRNAs in serum: a novel class of biomarkers for diagnosis of cancer and other diseases" *Cell Research*, 2008, 18:997-1006.

De Smaele E et al., "MicroRNAs as biomarkers for CNS cancer and other disorders" Brain Research, 2010, 1338:100-111.

Hansen T et al., "Brain Expressed microRNAs Implicated in Schizophrenia Etiology" *PLos One*, 2007, 9:e873.

Boissonneault V et al., "MicroRNA-298 and MicroRNA-328 Regulate Expression of Mouse_-Amyloid Precursor Protein-converting Enzyme 1" *The Journal of Biological Chemistry*, 2009, 284(4):1971-1981.

Sen CK et al., "Micromanaging Vascular Biology: Tiny MicroRNAs Play Big Band" *Journal of Vascular Research*, 2009, 46:527-540.

Urbich C et al., "Role of microRNAs in vascular diseases, inflammation, and angiogenesis" *Cardiovascular Research*, 2008, 79:581-588.

Jeong HC et al.,"Aberrant expression of let-7a miRNA in the blood of non-small cell lung cancer patients" *Molecular Medicine Reports*, 2011, 4:383-387.

Heneghan HM et al., "Circulating microRNAs as Novel Minimally Invasive Biomarkers for Breast Cancer" *Annals of Surgery*, 2010, 251(3):499-505.

Kim HK et al., "Muscle-specific microRNA miR-206 promotes muscle differentiation" *The Journal of Cell Biology*, 2006, 174(5):677-687.

Yanaihara N, et al., "Unique microRNA molecular profiles in lung cancer diagnosis and prognosis" *Cancer Cell*, 2006, 9:189-198.

Duroux-Richard I et al., "miRNAs and rheumatoid arthritis—promising novel biomarkers" *Swiss Medical Weekly*, 2011, 141:w13175.

Te JL et al., "Identification of Unique MicroRNA Signature Associated with Lupus Nephritis" *PLoS One*, 2010, 5(5):e10344.

Tijsen AJ et al., "MiR423-5p As a Circulating Biomarker for Heart Failure" *Circulation Research*, 2010, 106:1035-1039; originally published online Feb. 25, 2010.

Liu D-Z et al., "Brain and blood microRNA expression profiling of ischemic stroke, intracerebral hemorrhage, and kainate seizures" *Journal of Cerebral Blood Flow & Metabolism*, 2010, 30:92-101.

Fulci V et al., "miR-223 is overexpressed in T-lymphocytes of patients affected by rheumatoid arthritis" *Human Immunology*, 2010, 71:206-211.

Yu C-H et al., "Association of MicroRNA-223 Expression with Hepatic Ischemia/Reperfusion Injury in Mice" *Journal Digestive Diseases and Sciences*, 2009, 54:2362-2366.

Yao Y et al., "MicroRNA profiling of human gastric cancer" *Molecular Medicine Reports*, 2009, 2:963-970.

Li-Min L et al., "Serum microRNA Profiles Serve as Novel Biomarkers for HBV Infection and Diagnosis of HBV-Positive Hepatocarcinoma" Cancer Resesearch, 2010, 70:9798-9807. Published OnlineFirst Nov. 23, 2010.

Miyachi M et al., "Circulating muscle-specific microRNA, miR-206, as a potential diagnostic marker for rhabdomyosarcoma" *Biochemical and Biophysical Research Communications*, 2010, 400:89-93.

Wang X et al., "Cellular microRNA expression correlates with susceptibility of monocytes/macrophages to HIV-1 infection" *Blood*, 2009, 113:671-674.

Wang J-F et al., "Serum miR-146a and miR-223 as potential new biomarkers for sepsis" Biochemical and Biophysical Research Communications, 2010, 394:184-188.

Cogswell JP et al., "Identification of miRNA Changes in Alzheimer's Disease Brain and CSF Yields Putative Biomarkers and Insights into Disease Pathways" *Journal of Alzheimer's Disease*, 2008, 14:27-41.

Al J et al., "Circulating microRNA-1 as a potential novel biomarker for acute myocardial infarction" *Biochemical and Biophysical Research Communications*, 2010, 391:73-77.

Wang J et al., "MicroRNAs in Plasma of Pancreatic Ductal Adenocarcinoma Patients as Novel Blood-Based Biomarkers of Disease" *Cancer Prevention Research*, 2009, 2:807-813.

Ng Eko et al., "Differential expression of microRNAs in plasma of patients with colorectal cancer: a potential marker for colorectal cancer screening" *Gut*, 2009, 58:1375-1381.

Resnick KE et al., "The detection of differentially expressed microRNAs from the serum of ovarian cancer patients using a novel real-time PCR platform" Gynecologic Oncology, 2009, 112:55-59.

Skog J et al., "Glioblastoma microvesicles transport RNA and protein that promote tumor growth and provide diagnostic biomarkers" *Nature Cell Biology*, 2008, 10(12):1470-1476.

Mitchell, P. et al. "Circulating microRNAs as stable blood-based markers for cancer detection" *PNAS*, 2008, 105(30):10513-10518.

Gojo, S. et al. "In vivo cardiovasculogenesis by direct injection of isolated adult mesenchymal stem cells" *Exp. Cell Res.*, 2003, 288:51-59.

Wang, X. et al. "The role of the Sca-1+/CD31− cardiac progenitor cell population in postinfarction left ventricular remodeling" *Stem Cells*, 2006, 24:1779-1788.

Costa, F.F. et al. "Concise Review: Cancer/Testis Antigens, Stem Cells, and Cancer" *Stem Cells*, 2007, pp. 707-711, vol. 25.

Croce, C.M. and Calin, G.A. "miRNAs, Cancer, and Stem Cell Division" *Cell*, 2005, pp. 6-7, vol. 122.

Gaur, A. et al. "Characterization of MicroRNA Expression Levels and Their Biological Correlates in Human Cancer Cell Lines" *Cancer Research*, Mar. 15, 2007, pp. 2456-2468, vol. 67, No. 6.

Giangreco, A. et al. "Lung Cancer and Lung Stem Cells Strange Bedfellows?" *American Journal of Respiratory and Critical Care Medicine*, 2007, pp. 547-553, vol. 175.

Hatfield, S.D. et al. "Stem cell division is regulated by the microRNA pathway" *Nature*, Jun. 2005, pp. 974-978, vol. 435, No. 16.

Houbaviy, H.B. et al. "Embryonic Stem Cell-Specific MicroRNAs" *Developmental Cell*, Aug. 2003, pp. 351-358, vol. 5.

Kim, C.F.B. et al. "Identification of Bronchioalveolar Stem Cells in Normal Lung and Lung Cancer" *Cell*, Jun. 17, 2005, pp. 823-835, vol. 121.

Kumar, M.S. et al. "Impaired microRNA processing enhances cellular transformation and tumorigenesis" *Nature Genetics*, May 2007, pp. 673-677, vol. 39, No. 5.

Lee, E.J. et al. "Expression profiling identities microRNA signature in pancreatic cancer" *International Journal of Cancer*, 2006, pp. 1046-1054, vol. 120.

(56) References Cited

OTHER PUBLICATIONS

Lee, Y.S. et al. "The tumor suppressor microRNA *let-7* represses the HMGA2 oncogene" *Genes & Development*, 2007, pp. 1025-1030, vol. 21.

Lu, J. et al. "MicroRNA expression profiles classify human cancers" *Nature*, Jun. 2005, pp. 834-838, vol. 435, No. 9.

Michael, M.Z. et al. "Reduced Accumulation of Specific MicroRNAs n Colorectal Neoplasia" *Molecular Cancer Research*, Oct. 2003, pp. 882-891, vol. 1.

Oakley, E.J. and Van Zant, G. "Unraveling the complex regulation of stem cells: implications for aging and cancer" *Leukemia*, 2007, pp. 612-621, vol. 21.

Tysnes, B.B. and Bjerkvig, R. "Cancer initiation and progression: Involvement of stem cells and the microenvironment" *Biochimica et Biophysica Acta*, 2007, pp. 283-297, vol. 1775.

Wang, T. et al. "A Micro-RNA Signature Associated with Race, Tumor Size, and Target Gene Activity in Human Uterine Leiomyomas" *Genes, Chromosomes & Cancer*, 2007, pp. 336-347, vol. 46.

\* cited by examiner

MICRO-RNAS MODULATING IMMUNITY AND INFLAMMATION

CROSS REFERENCE TO RELATED APPLICATIONS

This application is a divisional of U.S. application Ser. No. 12/600,803, filed May 17, 2010, which is the National Stage of International Application Number PCT/US2008/064678, filed May 23, 2008, which claims the benefit of U.S. Provisional Patent Application No. 60/939,769, filed May 23, 2007, and U.S. Provisional Patent Application No. 60/939,902, filed May 24, 2007, the contents of which are herein incorporated by reference.

STATEMENT OF GOVERNMENT INTEREST

This invention was made with government support under Grant Nos. 1R41HL076964-01 and 1R41HL078298 awarded by the National Institutes for Health. The government has certain rights in the invention.

FIELD OF INVENTION

This invention relates to microRNA molecules associated with the regulation of gene expression. More specifically, this invention relates to microRNAs modulating immunity and inflammation and their use in diagnosis, prevention, and treatment of immune-related diseases in mammals, for example, humans, and further relates to screening methods to identify compounds and reagents useful in diagnosis, prevention, and therapy of immune-related diseases and inflammation.

BACKGROUND OF THE INVENTION

Asthma is a chronic disease that affects the airways of the respiratory system. In the United States, about 20 million people have been diagnosed with asthma, nearly half of those affected being children. The incidence of asthma is rising in developed countries, though there is great variation in incidence between countries and socioeconomic groups.

Episodes of asthma are characterized by a constriction of the airways, as the airways become inflamed and excessive amounts of mucus line the airways. Due to the narrowing of reactive airways, less air is able to flow to the lungs. This can result in wheezing, coughing, chest tightness, and trouble breathing, especially at night and in the early morning. The exact triggers for asthma are not clear-cut. Moreover, triggers may be due to a combination of factors. Recognized triggers include allergens (e.g. animal dander, dust mites, pollen, and mold), irritants (e.g. cigarette smoke, air pollution, cold air or changes in weather, strong odors such as those from painting or cooking, scented products or perfumes, moist air, exercise or exertion, or emotional stress), or other factors such as certain medicines (e.g. aspirin and beta-blockers), sulfites in food (dried fruit) or beverages (wine), gastroesophageal reflux, and infections. In children, the most common triggers are viral illnesses such as those that cause the common cold. The disease also has a significant genetic component.

The development of asthma involves many genes and environmental factors. An understanding of the genetic basis of the disease has great implications its management. To date, dozens of genes have been associated with asthma. Many of the genes are related to the immune system or to modulating inflammation. However, results have not been consistent among various populations studied, indicating that there is variation in the disease and not all genes are associated with asthma under every condition. The heterogeneity in the disease highlights the complex interactions causing the disease and the need for further study to fully understand the mechanisms involved.

The symptoms of asthma can range from mild to life threatening. Symptoms can usually be controlled with a combination of drugs and environmental changes. Treatment for asthma includes avoiding triggers, such as allergens and irritants, monitoring asthma and associated symptoms, and asthma medicines. Current asthma medicines include beta-agonists (bronchodilators), corticosteroids, theophylline and leukotriene modifiers.

SUMMARY OF THE INVENTION

MicroRNAs are shown to be up- and/or down-regulated in inflammation and immune cells using a mouse model of asthma and regulatory T cells as source of RNA, respectively. Modulating the expression of these microRNAs can be effective in redirecting inflammation and immunity and hence, may be beneficial as biomarkers or as therapeutic agents against diverse human immunologic and inflammatory diseases.

In a first aspect the present invention provides a method of screening asthma in a subject. The method includes the steps of assaying the miRNA expression level in a test sample of tissue from the subject to be screened for asthma, comparing the assayed the miRNA expression level to the miRNA expression level in a normal sample providing a control relative to the test sample of the subject, and computing the differential expression of the miRNA from the subject.

The assayed miRNA can be miR-765, miR-711, miR-690, miR-709, miR-762, miR-296, miR-671, miR-680, miR-760, miR-710, miR-320. miR-770-3p, miR-601, miR-577, miR-340, miR-326, miR-515-3p, miR-494, miR-142-3p, miR-705, miR-674, let-7f, miR-466, miR-540, miR-702, miR-584, miR-505, miR-17-3p, miR-721, miR-202, miR-564, miR-759, miR-638, miR-295, miR-325, miR-470, miR-573, miR-206, miR-298, miR-671, miR-198, miR-370, miR-320, miR-766, miR-610, let-7d, let-7b, let-7a, miR-150, miR-630, miR-185, miR-659, miR-625, miR-214, miR-493-3p, miR-296, miR-513, miR-768-5p, miR-637, miR-551a, let-7c, miR-542-5p, miR-320, miR-611, miR-381, miR-328, miR-518c, miR-27a, miR-608, miR-30d, hsa-miR-575, miR-21, and miR-658.

In an advantageous embodiment the at least one of the miRNAs assayed is an asthma-associated miRNA under-expressed in asthma. The under-expressed miRNA can be miR-690, miR-709, miR-762, miR-320, miR-494, miR-142-3p, let-7f, miR-550, miR-759, miR-573, miR-150, miR-214, miR-637, let7c, miR-381, miR-27a, and miR-575.

In another advantageous embodiment the at least one of the miRNAs assayed is an asthma-associated miRNA over-expressed in asthma. The over-expressed miRNA can be miR-760, miR-515-3p, and miR-671.

In a second aspect the present invention provides a method of identifying miRNA biomarkers of immunologic disease. The method includes the steps of generating an miRNA expression profile for a test sample representative of the immunologic disease, generating an miRNA expression profile for a control sample not exhibiting the disease condition, and comparing the miRNA expression profile of the test sample with the miRNA expression profile of control sample, wherein the differential expression of the miRNA identifies potential miRNA biomarkers for immunologic disease.

In a third aspect the present invention provides a method of identifying miRNA biomarkers of inflammation. The method includes the steps of contacting a sample or sample tissue with an agent to induce an inflammatory response in the sample or sample tissue, generating an miRNA expression profile for the sample contacted with the agent, generating an miRNA expression profile for a control sample not contacted with the agent, and comparing the miRNA expression profile of the sample with an miRNA expression profile of a sample not contacted with the agent. The differential expression of the miRNA in the sample contacted with the agent identifies potential miRNA biomarkers for the inflammation.

In a fourth aspect the present invention provides a method for identifying miRNA biomarkers of asthma in a subject. The method includes the steps of contacting a sample of the subject with an asthma-trigger agent, generating an miRNA expression profile for the sample contacted with the agent, generating an miRNA expression profile for a control sample not contacted with the asthma trigger agent, and comparing the miRNA expression profile of the sample with an miRNA expression profile of a sample not contacted with the candidate asthma-trigger agent. The differential expression of the miRNA in the sample contacted with the agent identifies potential miRNA biomarkers for the subject.

In a fifth aspect the present invention provides a method for identifying asthma-trigger agents in a subject. The method includes the steps of contacting a tissue sample from the subject with a candidate asthma-trigger agent, assaying the resulting miRNA expression level in the contacted tissue, comparing the miRNA expression profile of the contacted tissue sample with an miRNA expression profile of a sample not contacted with the candidate asthma-trigger agent, wherein the differential expression of the miRNA in the sample contacted with the agent identifies potential asthma trigger agents for the subject.

The assayed miRNA can include miR-765, miR-711, miR-690, miR-709, miR-762, miR-296, miR-671, miR-680, miR-760, miR-710, miR-320. miR-770-3p, miR-601, miR-577, miR-340, miR-326, miR-515-3p, miR-494, miR-142-3p, miR-705, miR-674, let-7f, miR-466, miR-540, miR-702, miR-584, miR-505, miR-17-3p, miR-721, miR-202, miR-564, miR-759, miR-638, miR-295, miR-325, miR-470, miR-573, miR-206, miR-298, miR-671, miR-198, miR-370, miR-320, miR-766, miR-610, let-7d, let-7b, let-7a, miR-150, miR-630, miR-185, miR-659, miR-625, miR-214, miR-493-3p, miR-296, miR-513, miR-768-5p, miR-637, miR-551a, let-7c, miR-542-5p, miR-320, miR-611, miR-381, miR-328, miR-518c, miR-27a, miR-608, miR-30d, hsa-miR-575, miR-21, and miR-658.

In an advantageous embodiment the at least one of the miRNAs assayed is an asthma-associated miRNA under-expressed in asthma. The under-expressed miRNA can be miR-690, miR-709, miR-762, miR-320, miR-494, miR-142-3p, let-7f, miR-550, miR-759, miR-573, miR-150, miR-214, miR-637, let7c, miR-381, miR-27a, and miR-575.

In another advantageous embodiment the at least one of the miRNAs assayed is an asthma-associated miRNA over-expressed in asthma. The over-expressed miRNA can be miR-760, miR-515-3p, and miR-671.

In a sixth aspect the present invention provides a method for screening for candidate asthma therapeutic agents. The method includes the steps of assaying miRNA expression levels in a control sample to determine baseline miRNA expression levels for the sample, contacting a test sample with one or more therapeutic agents and one or more asthma-trigger agents, assaying the resulting miRNA expression level in the test sample, comparing the miRNA expression level in the test sample to the baseline miRNA expression level to determine the treated miRNA deviation, contacting a control sample with the one or more asthma-trigger agents, assaying the resulting miRNA expression level in the control sample to determine an exposed control, comparing the miRNA expression level in the exposed control to the baseline miRNA expression level to determine the exposed miRNA deviation, and comparing the treated miRNA deviation with the exposed miRNA deviation, wherein a reduced deviation in the treated miRNA deviation relative to the exposed miRNA deviation identifies a candidate asthma therapeutic agent.

The assayed miRNA can be miR-765, miR-711, miR-690, miR-709, miR-762, miR-296, miR-671, miR-680, miR-760, miR-710, miR-320. miR-770-3p, miR-601, miR-577, miR-340, miR-326, miR-515-3p, miR-494, miR-142-3p, miR-705, miR-674, let-7f, miR-466, miR-540, miR-702, miR-584, miR-505, miR-17-3p, miR-721, miR-202, miR-564, miR-759, miR-638, miR-295, miR-325, miR-470, miR-573, miR-206, miR-298, miR-671, miR-198, miR-370, miR-320, miR-766, miR-610, let-7d, let-7b, let-7a, miR-150, miR-630, miR-185, miR-659, miR-625, miR-214, miR-493-3p, miR-296, miR-513, miR-768-5p, miR-637, miR-551a, let-7c, miR-542-5p, miR-320, miR-611, miR-381, miR-328, miR-518c, miR-27a, miR-608, miR-30d, hsa-miR-575, miR-21, and miR-658.

In a seventh aspect the present invention provides a method for treating inflammation or an immunologic disorder. The method includes the steps of contacting a cell or cells with an agent that modulates the expression of one or more miRNA in the cell.

In certain embodiments the agent is an agent that upregulates the expression of at least one of the one or more miRNA. In further embodiments thereof the agent is a vector comprising an miRNA sequence, or a derivative or analog thereof, underexpressed in the associated disease. The underexpressed miRNA can be miR-690, miR-709, miR-762, miR-320, miR-494, miR-142-3p, let-7f, miR-550, miR-759, miR-573, miR-150, miR-214, miR-637, let7c, miR-381, miR-27a, and miR-575.

In alternative embodiments the agent is an agent that downregulates the expression of at least one of the one or more miRNA. In further embodiments thereof the agent is a vector comprising an miRNA sequence, or a derivative or analog thereof, overexpressed in the associated disease. The overexpressed miRNA can be miR-760, miR-515-3p, and miR-671. The agent can be an antisense RNA to the overexpressed miRNA.

The treated immunologic disorder can be asthma.

BRIEF DESCRIPTION OF THE DRAWINGS

For a fuller understanding of the invention, reference should be made to the following detailed description, taken in connection with the accompanying drawings, in which:

In FIG. 19(B) cells were separated from the mice spleens, their RNA isolated and subjected to miRNA dot array.

(FIG. 21—top) Linear amplification plot of the miRNA Q-PCR assay, showing robotic exponent amplification of the miRNA replicons and sensitivity over 3×104 times of magnitude. The experiments were conducted in duplicate. (FIG. 21—bottom) Dissociation curves of all the miRNA amplicons, indicating specific amplification of miRNAs.

(FIG. 22) & (FIG. 23) Expression levels of five miRNAs in asthmatic (OVA) relative to that of the corresponding miRNAs in control (PBS). (FIG. 22) Regular RT PCR.

FIG. 23 shows PCR validation of the dot-blot array data. (FIG. 22) & (FIG. 23) Expression levels of five miRNAs in asthmatic (OVA) relative to that of the corresponding miRNAs in control (PBS). (FIG. 22) Regular RT PCR; (FIG. 23) Q-PCR.

(FIG. 24) Lung histological features of mice that were sensitized, then treated with vehicle control (n=4) (top), or miRRA-1 (n=4) (bottom) before challenged with OVA (n=4). The infiltrates in the bronchovascular bundles of these animals are illustrated. Original magnification, ×100.

FIG. 25 shows the inhibition of OVA-induced lung inflammation by miRRA-1. 25 μg of miRRA-1 or control miRNA (scrambled) plasmid DNA were delivered i.n. into the lung of each sensitized Balb/C mouse by using nanoparticle NG042 for three consecutive days before OVA challenge. 24 hr after challenge, mice were sacrificed and half of the lung was fixed and subjected to H & E staining; another half was used for CBA cytokine assay. (FIG. 24) Lung histological features of mice that were sensitized, then treated with vehicle control (n=4) (top), or miRRA-1 (n=4) (bottom) before challenged with OVA (n=4). The infiltrates in the bronchovascular bundles of these animals are illustrated. Original magnification, ×100.

(FIG. 27) Cell proliferation assay of Jurkat cells infected with lentiviruses of miRRA1 or control miRNA by using the CyQUANT® NF Cell Proliferation Assay Kit. About 1,000-6,000 lentivirue-infectd cells were plated into 96-wellmicroplate wells 4 hours before assay. The fluorescence intensity of each sample was measured by using a fluorescence microplate reader (Synergy™ HT Multi-Detection Microplate Reader from Biotek) with excitation at ~485 nm and emission detection at ~530 nm.

(FIG. 28) Growth cuve assay of HeLa cells stably transfected with the vectors that overexpress miRNA1 or control scramble miRNA.

(FIG. 29) Colony-forming assay of A549 cells after transfected with the vectors that overexpress miRNA1 or control scramble miRNA.

(FIG. 30) Hsa-miRRA1 increases caspase 3/7 activity in A549 cells induced by staurosporine. A549 cells were plated in 96-well plates and allowed to attach for 10 hours at 37° C./5% CO2. Apoptosis was induced by treating with various doses of staurosporine for 16 hours at 37° C./5% CO2. Plates were incubated at room temperature, and luminescence was recorded using a Bioteck Microplate Reader. Relative luciferase activity (RLU).

(FIG. 31). Western blot.

(FIG. 32) Density of each band.

DETAILED DESCRIPTION OF THE PREFERRED EMBODIMENT

Figure 1:
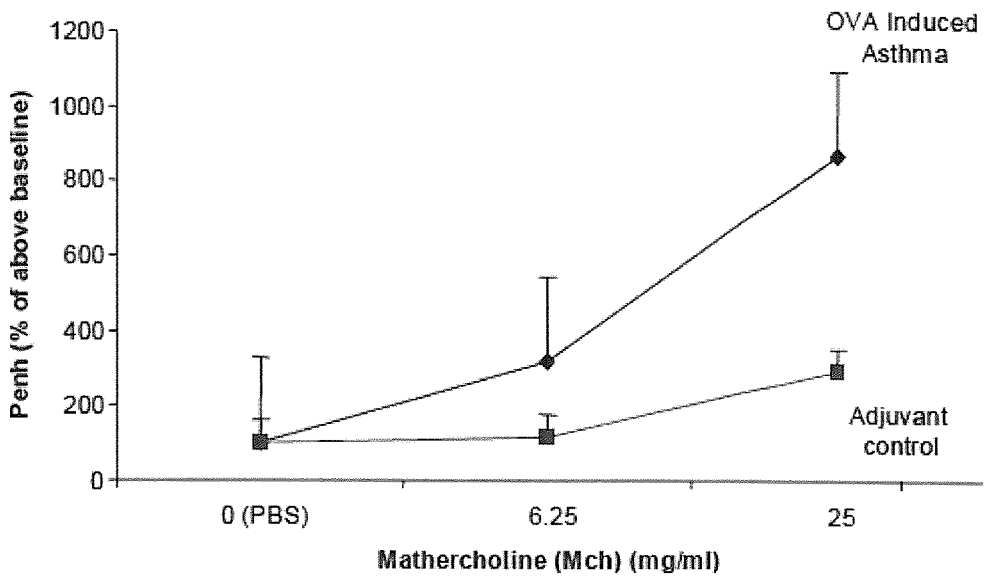
FIG. 1 is a graph showing airway hyperreactivity in a chronic asthma mouse model.

MicroRNAs (miRNA) are small (about 18 to 25 bp) non-coding RNAs that negatively regulate mRNA translation on a sequence-specific manner. Like protein-coding mRNA, miRNA precursors are transcribed by RNA polymerase II, spliced and polyadenylated. However, unlike mRNA, miRNA precursors will be further processed into functional single-stranded 'mature' miRNAs. The mature miRNA then guides a complex called miRISC (miRNA induced silence complex) to its target mRNA to block the translation. (Croce, C. M. and Calin, G. A., *Cell* (2005) 122, 6-7) To date, 474 human miRNAs and 377 mouse miRNA have been identified according to the miRNA database miRBase (http://microrna.sanger.ac.uk/). It is believed that the number of miRNAs could exceed 1000, which constitute approximately 1-5% of the expressed genes. Bioinformatics analyses suggest that, on average, each miRNA may regulate about 200 genes. Therefore, as much as 30% to 50% of all human genes may be under miRNA control. MiRNAs are important negative regulators of many if not all human genes and thus involved in many if not all cellular processes. Moreover, the levels of individual miRNAs are dramatically changed in different cell types and developmental stages, suggesting that miRNA may play profound and pervasive roles in cell development, proliferation and apoptosis. Correspondingly, their expression patterns are highly regulated. Deregulation of miRNA function might contribute to many human diseases including tumorigenesis.

Expression profiling of miRNA in numerous human cancer cell lines and primary cancers demonstrates that aberrant miRNA expression is a hallmark of tumor development. (Gaur, A. et al., *Cancer Res* (2007) 67: 2456-68) Aberrant expression of specific miRNA genes contributes to the initiation and progression of cancer, suggesting that miRNA genes could function as potential oncogenes and repressors in the human body. (Lee, Y. S. and Dutta, A., The tumor suppressor microRNA let-7 represses the HMGA2 oncogene. (2007) *Genes Dev*; Croce, C. M. and Calin, G. A., *Cell* (2005) 122: 6-7) Recent work has shown that there is a global decrease of miRNA expression in human cancers compared with normal tissues, and global repression of miRNA maturation promotes cellular transformation and tumorigenesis, suggesting that global miRNA loss may enhance tumorigenesis. (Kumar, M. S., et al., Impaired microRNA processing enhances cellular transformation and tumorigenesis. *Nat Genet* (2007) Impaired microRNA processing enhances cellular transformation and tumorigenesis.

Moreover, accumulated evidences show that miRNAs may serve as a fine tuner of gene expression. For example, miRNA profiling has been successfully used to classify different cancers including poorly differentiated tumors and different cell lineages, whereas mRNA profiles were highly inaccurate when applied to the same samples; subsets of miRNAs were strongly associated with tumor sizes and race. (Wang, T. et al., *Genes Chromosomes Cancer* (2007) 46: 336-47) These findings highlight that the expression pattern of miRNA profiling can be of greater value than that of 13,000 protein-encoding genes in cancer diagnosis and prognosis. Lu, J. et al., *Nature* (2005) 435: 834-8; Michael, M. Z., et al., *Mol Cancer Res* (2003) 1: 882-91; Lee, E. J. et al., *Int J Cancer* (2007) 120: 1046-54) It appears that miRNAs are so far the best molecular signatures for development and tumorigenesis.

The human Bic/miRNA-155 gene, which is 96% identical with the mature mouse microRNA, is located in a region of chromosome 21 associated with asthma, pollen sensitivity and atopic dermatitis. Hence it is thought that the equivalent human microRNA may be linked with the onset of some immune diseases. FoxP3 directly direct the transcription of mir-155.

These compelling data have demonstrated that miRNA may play an important role in tumorigenesis. However, all these studies were conducted on tumors that are usually highly heterogeneous, cancer cells in the same tumor may have different miRNA expression patterns from each other, and the results may be a mixture of different miRNA expression patterns. Recent findings suggest that tumor heterogeneity may be a result of the differentiation of a few cancer stem cells (CSCs), which have been described in acute myeloid leukemia, breast, brain, bone, lung, melanoma and prostate. (Tysnes, B. B. & Bjerkvig, R., Cancer initiation and progression: Involvement of stem cells and the microenvironment. *Biochim Biophys Acta* (2007)) This concept has profound implications both in cancer theory and cancer therapy. Based on this concept, tumors are originated from a few cancer stem cells, which are responsible for tumor growth and metastasis. Therefore, specifically targeting CSCs may be more efficient at inhibiting cancer growth and metastasis, and studying miRNA in CSCs may greatly further our understanding of tumorigenesis. However, miRNA has not been explored in CSCs.

Recent findings show that miRNAs are required for cell division and pluripotency maintenance of normal stem cells. (Hatfield, S. D. et al. *Nature* (2005) 435: 974-8; Houbaviy, H. B., et al., *Dev Cell* (2003) 5: 351-8) CSCs are very similar to their counterpart normal stem cells in many aspects, and there is strong evidence show that CSC are derived from normal stem cells that have gradually accumulated various genetic and epigenetic defects as a result of a general loss of repression, decreased expression of miRNA genes, resulting in uncontrolled proliferation. (Tysnes, B. B. & Bjerkvig, R., Cancer initiation and progression: Involvement of stem cells and the microenvironment. *Biochim Biophys Acta* (2007); Costa, F. F., et al., *Stem Cells* (2007) 25: 707-11; Giangreco, A., et al. *Am J Respir Crit Care Med* (2007) 175: 547-53; Oakley, E. J. & Van Zant, G., *Leukemia* (2007) 21: 612-21) Normal lung BSCs can directly act as originating cells for bronchoalveolar carcinomas. (Kim, C. F. et al. *Cell* (2005) 121: 823-35).

MicroRNAs (miRNAs) are short (~22 nt) non-coding RNAs that regulate gene expression in a quick and accurate manner by targeting hundreds of genes per miRNA in response to environmental and internal signals. MiRNAs are involved in a remarkable spectrum of biological pathways and are well suited for studying complex human diseases such as asthma. Successful immunotherapy appears to result in increased number of T regulatory cells (Treg), which inhibit activation of Th2 and Th1 cells. This suggests that the lack of Treg cells promotes asthma pathogenesis.1 It is hypothesized that miRNA may play a critical role in controlling pathogenesis of asthma, by regulating the function of Treg and TH2 cells.

Sample

The present invention provides a method of detection, classification, diagnosis or prognosis of inflammation, immunologic disease or disorder, or hyperproliferative diseases on at least one sample obtained from an individual. The individual may be any mammal, but is preferably a human. The individual may be any individual, an individual predisposed of a disease or an individual suffering from a disease.

A sample as defined herein is a small part of an individual, representative of the whole and may be constituted by a biopsy or a body fluid sample. Biopsies are small pieces of tissue and may be fresh, frozen or fixed, such as formalin-fixed and paraffin embedded (FFPE). Body fluid samples may be blood, plasma, serum, urine, sputum, cerebrospinal fluid, milk, or ductal fluid samples and may likewise be fresh, frozen or fixed. Samples may be removed surgically, by extraction i.e. by hypodermic or other types of needles, by microdissection or laser capture.

As the object of the present invention regards inflammation, immunologic disease or disorder, or hyperproliferative diseases, obtaining more than one sample, such as two samples, such as three samples, four samples or more from individuals, and preferably the same individual, is of importance. The at least two samples may be taken from normal tissue and hyperproliferative tissue, respectively. This allows the relative comparison of expression both as in the presence or absence of at least one nucleic acid and/or the level of expression of the at least one nucleic acid between the two samples. Alternatively, a single sample may be compared against a "standardized" sample, such a sample being a sample comprising material or data from several samples, preferably also from several individuals. A standardized sample may comprise either normal or hyperproliferative sample material or data.

With respect to hyperproliferative disorders, In a preferred embodiment of the present invention the method of detection, classification, diagnosis or prognosis is performed on a biopsy. In a more preferred embodiment of the present invention the method of detection, classification, diagnosis or prognosis is performed on a body fluid sample such as a blood sample or a ductal fluid sample. Ductal fluid samples may be from nipple aspirates or ductal lavage.

Sample Preparation

Before analyzing the sample, it will often be desirable to perform one or more sample preparation operations upon the sample. Typically, these sample preparation operations will include such manipulations as concentration, suspension, extraction of intracellular material, e.g., nucleic acids from tissue/whole cell samples and the like, amplification of nucleic acids, fragmentation, transcription, labelling and/or extension reactions.

Nucleic acids, especially RNA and specifically miRNA can be isolated using any techniques known in the art. There are two main methods for isolating RNA: phenol-based extraction and silica matrix or glass fiber filter (GFF)-based binding. Phenol-based reagents contain a combination of denaturants and RNase inhibitors for cell and tissue disruption and subsequent separation of RNA from contaminants. Phenol-based isolation procedures can recover RNA species in the 10-200-nucleotide range e.g., miRNAs, 5S rRNA, 5.8S rRNA, and U1 snRNA. If a sample of "total" RNA was purified by the popular silica matrix column or GFF procedure, it may be depleted in small RNAs. Extraction procedures such as those using Trizol or TriReagent, however will purify all RNAs, large and small, and are the recommended methods for isolating total RNA from biological samples that will contain miRNAs/siRNAs.

Any method required for the processing of a sample prior to detection by any of the herein mentioned methods falls within the scope of the present invention. These methods are typically well known by a person skilled in the art.

Detection

It is within the general scope of the present invention to provide methods for the detection of miRNA. An aspect of the present invention relates to the detection of the miRNA sequences of as described in the plots and graphs of the figures contained herein. By detection is meant both 1) detection in the sense of presence versus absence of one or more miRNAs as well as 2) the registration of the level or degree of expression of one or more miRNAs, depending on the method of detection employed.

The detection of one or more nucleic acid molecules allows for the classification, diagnosis and prognosis of a disease such as a immunologic disease, e.g. a hypersensitivity associated with asthma, alternatively inflammatory disease. The classification of a disease is of relevance both medically and scientifically and may provide important information useful for the diagnosis, prognosis and treatment of the disease. The diagnosis of a disease is the affirmation of the presence of the disease based, as is the object of the present invention, on the expression of at least one miRNA or miRNA precursor molecule herein also referred to as a nucleic acid molecule. Prognosis is the estimate or prediction of the probable outcome of a disease and the prognosis of a disease is greatly facilitated by increasing the amount of information on the particular disease. The method of detection is thus a central aspect of the present invention.

Any method of detection falls within the general scope of the present invention. The detection methods may be generic for the detection of nucleic acids especially RNA, or be optimized for the detection of small RNA species, as both mature and precursor miRNAs fall into this category or be specially designed for the detection of miRNA species. The detection methods may be directed towards the scoring of a presence or absence of one or more nucleic acid molecules or may be useful in the detection of expression levels.

The detection methods can be divided into two categories herein referred to as in situ methods or screening methods. The term in situ method refers to the detection of nucleic acid molecules in a sample wherein the structure of the sample has been preserved. This may thus be a biopsy wherein the structure of the tissue is preserved. In situ methods are generally histological i.e. microscopic in nature and include but are not limited to methods such as: in situ hybridization techniques and in situ PCR methods.

Screening methods generally employ techniques of molecular biology and most often require the preparation of the sample material in order to access the nucleic acid molecules to be detected. Screening methods include, but are not limited to methods such as: Array systems, affinity matrices, Northern blotting and PCR techniques, such as real-time quantitative RT-PCR.

Probe

It is an object of the present invention to provide a probe which can be used for the detection of a nucleic acid molecule as defined herein. A probe as defined herein is a specific sequence of a nucleic acid used to detect nucleic acids by hybridization. A nucleic acid is also here any nucleic acid, natural or synthetic such as DNA, RNA, LNA or PNA. A probe may be labeled, tagged or immobilized or otherwise modified according to the requirements of the detection method chosen. A label or a tag is an entity making it possible to identify a compound to which it is associated. It is within the scope of the present invention to employ probes that are labeled or tagged by any means known in the art such as but not limited to: radioactive labeling, fluorescent labeling and enzymatic labeling. Furthermore the probe, labeled or not, may be immobilized to facilitate detection according to the detection method of choice and this may be accomplished according to the preferred method of the particular detection method.

Detection Methods

An aspect of the present invention regards the detection of nucleic acid molecules by any method known in the art. In the following are given examples of various detection methods that can be employed for this purpose, and the present invention includes all the mentioned methods, but is not limited to any of these.

In Situ Hybridization

In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/across cells, such as the expression of miRNAs/nucleic acid molecules as herein described.

Sample cells are treated to increase their permeability to allow the probe to enter the cells, the probe is added to the treated cells, allowed to hybridize at pertinent temperature, and then excess probe is washed away. A complementary probe is labeled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe based upon the miRNAs mentioned herein.

An embodiment of the present invention regards the method of detection by in situ hybridization as described herein.

In Situ PCR

In situ PCR is the PCR based amplification of the target nucleic acid sequences prior to ISH. For detection of RNA, an intracellular reverse transcription (RT) step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labelld nucleotides (e.g. digoxigenin-11-dUTP, fluorescein-dUTP, 3H-CTP or biotin-16-dUTP) which have been incorporated into the PCR products during thermal cycling.

An embodiment of the present invention regards the method of in situ PCR as mentioned herein above for the detection of nucleic acid molecules as detailed herein.

Microarray

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used e.g. to measure the expression levels of large numbers of mRNAs/miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

An aspect of the present invention regards the use of microarrays for the expression profiling of miRNAs in immunologic diseases/disorders or inflammation. For this purpose, and by way of example, RNA is extracted from a cell or tissue sample, the small RNAs (18-26-nucleotide RNAs) are size-selected from total RNA using denaturing polyacrylamide gel electrophoresis (PAGE). Then oligonucleotide linkers are attached to the 5' and 3' ends of the small RNAs and the resulting ligation products are used as templates for an RT-PCR reaction with 10 cycles of amplification. The sense strand PCR primer has a Cy3 fluorophore attached to its 5' end, thereby fluorescently labelling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

Alternatively, total RNA containing the small RNA fraction (including the miRNA) extracted from a cell or tissue sample is used directly without size-selection of small RNAs, and 3' end labeled using T4 RNA ligase and either a Cy3- or Cy5-labeled short RNA linker (f. ex. 5'-PO4-rUrUrU-Cy3/dT-3' or 5'-PO4-rUrUrU-Cy5/dT-3'). The RNA samples are labelled by incubation at 30° C. for 2 hours followed by heat inactivation of the T4 RNA ligase at 80° C. for 5 minutes. The fluorophore-labelled miRNAs complementary to the corresponding miRNA capture probe sequences on the array will hybridize, via base pairing, to the spot at which the capture probes are affixed. The microarray scanning and data processing is carried out as above.

Several types of microarrays can be employed such as spotted oligonucleotide microarrays, pre-fabricated oligonucleotide microarrays or spotted long oligonucleotide arrays.

In spotted oligonucleotide microarrays the capture probes are oligonucleotides complementary to miRNA sequences. This type of array is typically hybridized with amplified PCR products of size-selected small RNAs from two samples to be compared (e.g. hyperproliferative and normal samples from an individual) that are labelled with two different fluorophores. Alternatively, total RNA containing the small RNA fraction (including the miRNAs) is extracted from the above-mentioned two samples and used directly without size-selection of small RNAs, and 3' end labeled using T4 RNA ligase and short RNA linkers labelled with two different fluorophores. The samples can be mixed and hybridized to one single microarray that is then scanned, allowing the visualization of up-regulated and down-regulated miRNA genes in one go. The downside of this is that the absolute levels of gene expression cannot be observed, but the cost of the experiment is reduced by half. Alternatively, a universal reference can be used, comprising of a large set of fluorophore-labelled oligonucleotides, complementary to the array capture probes.

In pre-fabricated oligonucleotide microarrays or single-channel microarrays, the probes are designed to match the sequences of known or predicted miRNAs. There are commercially available designs that cover complete genomes from companies such as Affymetrix, or Agilent. These microarrays give estimations of the absolute value of gene expression and therefore the comparison of two conditions requires the use of two separate microarrays.

Spotted long Oligonucleotide Arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

An embodiment of the present invention regards the method of microarray use and analysis as described herein.

A preferred embodiment of the present invention regards the use of microarrays for the expression profiling of miRNAs in immunologic diseases such as hypersensitivity and especially asthma, as well as other inflammatory conditions.

PCR

The terms "PCR reaction", "FOR amplification", "PCR", "pre-PCR", "Q-PCR", "real-time quantitative FOR" and "real-time quantitative RT-PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification and Q Beta Replicase systems. The products formed by said amplification reaction may or may not be monitored in real time or only after the reaction as an end-point measurement.

Real-Time Quantitative RT-PCR

Real-time quantitative RT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample. There are 3 methods which vary in difficulty and detail. Like other forms of polymerase chain reaction, the process is used to amplify DNA samples, using thermal cycling and a thermostable DNA polymerase.

The three commonly used methods of quantitative polymerase chain reaction are through agarose gel electrophoresis, the use of SYBR Green, a double stranded DNA dye, and the fluorescent reporter probe. The latter two of these three can be analysed in real-time, constituting real-time polymerase chain reaction method.

Agarose gel electrophoresis is the simplest method, but also often slow and less accurate then other methods, depending on the running of an agarose gel via electrophoresis. It cannot give results in real time. The unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown. This method is generally used as a simple measure of whether the probe target sequences are present or not, and rarely as 'true' Q-PCR.

Using SYBR Green dye is more accurate than the gel method, and gives results in real time. A DNA binding dye binds all newly synthesized double stranded (ds)DNA and an increase in fluorescence intensity is measured, thus allowing initial concentrations to be determined. However, SYBR Green will label all dsDNA including any unexpected PCR products as well as primer dimers, leading to potential complications and artefacts. The reaction is prepared as usual, with the addition of fluorescent dsDNA dye. The reaction is run, and the levels of fluorescence are monitored; the dye only fluoresces when bound to the dsDNA. With reference to a standard sample or a standard curve, the dsDNA concentration in the PCR can be determined.

The fluorescent reporter probe method is the most accurate and most reliable of the methods. It uses a sequence-specific nucleic acid based probe so as to only quantify the probe sequence and not all double stranded DNA. It is commonly carried out with DNA based probes with a fluorescent reporter and a quencher held in adjacent positions, so-called dual-labelled probes. The close proximity of the reporter to the quencher prevents its fluorescence; it is only on the break-down of the probe that the fluorescence is detected. This process depends on the 5' to 3' exonuclease activity of the polymerase involved. The real-time quantitative PCR reaction is prepared with the addition of the dual-labelled probe. On denaturation of the double-stranded DNA template, the probe is able to bind to its complementary sequence in the region of interest of the template DNA (as the primers will too). When the PCR reaction mixture is heated to activate the polymerase, the polymerase starts synthesizing the complementary strand to the primed single stranded template DNA. As the polymerisation continues it reaches the probe bound to its complementary sequence, which is then hydrolysed due to the 5'-3' exonuclease activity of the polymerase thereby separating the fluorescent reporter and the quencher molecules. This results in an increase in fluorescence, which is detected. During thermal cycling of the real-time PCR reaction, the increase in fluorescence, as released from the hydrolysed dual-labelled probe in each PCR cycle is monitored, which allows accurate determination of the final, and so initial, quantities of DNA.

Any method of PCR that can determine the expression of a nucleic acid molecule as defined herein falls within the scope of the present invention. A preferred embodiment of the present invention regards the real-time quantitative RT-PCR method, based on the use of either SYBR Green dye or a dual-labelled probe for the detection and quantification of nucleic acids according to the herein described. A more preferred embodiment of the present invention regards the methods of real-time quantitative RT-PCR for the expression profiling of miRNAs in immunologic diseases such as hypersensitivity and asthma.

Northern Blot Analysis

An aspect of the present invention regards the detection of the nucleic acid molecules herein disclosed by the classical and to the art well-known technique of Northern blot analysis. Many variations of the protocol exist.

Pharmaceutical Composition

"Pharmaceutical agent, drug or composition" refers to any chemical or biological material, compound, or composition capable of inducing a desired prophylactic or therapeutic effect when properly administered to a patient. Some drugs are sold in an inactive form that is converted in vivo into a metabolite with pharmaceutical activity. For purposes of the present invention, the terms "pharmaceutical agent, drug or composition" encompass both the inactive drug and the active metabolite or derivate.

A pharmaceutical composition of the invention is formulated to be compatible with its intended route of administration and may thus comprise a pharmaceutically acceptable carrier. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene-diamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

A therapeutically effective amount of a composition containing a composition of the invention is an amount that is capable of modulating the expression of a pre-miRNA, miRNA or the target of a miRNA according to the herein described. Certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

Vehicles

Aspects of the present invention relate to various vehicles comprising the nucleic acid molecules of the present invention. By vehicle is understood an agent with which genetic material can be transferred. Herein such vehicles are exemplified as nucleic acid constructs, vectors, and delivery vehicles such as viruses and cells.

Nucleic Acid Construct

By nucleic acid construct is understood a genetically engineered nucleic acid. The nucleic acid construct may be a non-replicating and linear nucleic acid, a circular expression vector, an autonomously replicating plasmid or viral expression vector. A nucleic acid construct may comprise several elements such as, but not limited to genes or fragments of same, promoters, enhancers, terminators, poly-A tails, linkers, markers and host homologous sequences for integration. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989).

Several nucleic acid molecules may be encoded within the same construct and may be linked by an operative linker. By the term operative linker is understood a sequence of nucleotides two parts of a nucleic acid construct in a manner securing the biological processing of the encoded nucleic acid molecules.

Promoter

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. Depending on the promoter, it appears that individual elements can function either cooperatively or independently to activate transcription. Any promoter that can direct transcription initiation of the sequences encoded by the nucleic acid construct may be used in the invention.

An aspect of the present invention comprises the nucleic acid construct wherein the sequence of at least one nucleic acid molecule is preceded by a promoter enabling expression of the at least one nucleic acid molecule.

It is a further aspect that the promoter is selected from the group of constitutive promoters, inducible promoters, organism specific promoters, tissue specific promoters and cell type specific promoters. Examples of promoters include, but are not limited to: constitutive promoters such as: simian virus 40 (SV40) early promoter, a mouse mammary tumour virus promoter, a human immunodeficiency virus long terminal repeat promoter, a Moloney virus promoter, an avian leukaemia virus promoter, an Epstein-Barr virus immediate early promoter, a Rous sarcoma virus (RSV) promoter, a human actin promoter, a human myosin promoter, a human haemoglobin promoter, cytomegalovirus (CMV) promoter and a human muscle creatine promoter, inducible promoters such as: a metallothionine promoter, a glucocorticoid promoter, a progesterone promoter, and a tetracycline promoter (tet-on or tet-off), tissue specific promoters such as: HER-2 promoter and PSA associated promoter.

Delivery Vehicle

An aspect of the present invention comprises the nucleic acid construct as described in any of the above, comprised within a delivery vehicle. A delivery vehicle is an entity whereby a nucleotide sequence can be transported from at least one media to another. Delivery vehicles are generally used for expression of the sequences encoded within the nucleic acid construct and/or for the intracellular delivery of the construct. It is within the scope of the present invention that the delivery vehicle is a vehicle selected from the group of: RNA based vehicles, DNA based vehicles/vectors, lipid based vehicles, virally based vehicles and cell based vehicles. Examples of such delivery vehicles include, but are not limited to: biodegradable polymer microspheres, lipid based formulations such as liposome carriers, coating the construct onto colloidal gold particles, lipopolysaccharides, polypeptides, polysaccharides, pegylation of viral vehicles.

A preferred embodiment of the present invention comprises a virus as a delivery vehicle, where the virus is selected from the non-exhaustive group of: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art.

Treatment

The present invention further provides for compositions and methods for treating an individual having or at risk of acquiring a disease or disorder. Treatment includes prophylaxis and/or therapy. The disease may be characterized or caused by the overexpression or overactivity of a gene product, or alternatively, may be caused by the expression or activity of a mutant gene or gene product. The disease may thus be any of the herein mentioned diseases such as immunologic diseases such as hypersensitivty and especially asthma, or alternatively inflammation or hyperproliferative diseases.

The present invention provides for both prophylactic and therapeutic methods of treating a subject at risk of or susceptible to, a disease or having a disease associated with aberrant or unwanted target gene expression or activity. Another aspect of the invention pertains to methods of modulating target gene expression, gene product expression or activity for therapeutic purposes. Accordingly, in an exemplary embodiment, the modulatory method of the invention involves contacting a cell capable of expressing a target miRNA or the target mRNA of an miRNA with a therapeutic agent (e.g. a nucleic acid molecule as described herein) that is specific for the target gene or gene product (e.g. a nucleic acid molecule as described herein) such that expression or one or more of the activities of the target is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene product or nucleic acid molecule. Inhibition of target gene activity is desirable in situations in which the target gene is abnormally unregulated and/or in which decreased target gene activity is likely to have a beneficial effect.

An aspect of the present invention relates to the treatment of diseases characterized by the upregulation and/or downregulation of miRNAs. Such treatments may comprise administering nucleic acid molecules of the present invention in order to downregulate the miRNAs and/or upregulate the targets of said miRNAs. A preferred embodiment of the present invention relates to treatments counteracting the upregulation of miR-760, miR-515-3p, and miR-671 when these are associated with inflammation, immunologic disorder or hyperproliferative diseases. It is further contemplated that other molecules described herein as upregulated can similarly be used in treatment, diagnosis or screening methods. Similarly, it is contemplated that the results herein described for murine miRNAs (using the mmu prefix) can can be applied to the human counterpart miRNA (using the has prefix). Such treatment may comprise the administration of inhibitory agents e.g. anti-sense molecules, to directly interact with the overexpressed miRNAs.

Another preferred embodiment of the present invention relates to the treatment of diseases characterized by the downregulation of miRNAs. Such treatments may comprise administering nucleic acid molecules of the present invention in order to upregulate the miRNAs and/or downregulate the targets of said miRNAs. A preferred embodiment of the present invention relates to treatments counteracting the downregulation of miR-690, miR-709, miR-762, miR-320, miR-494, miR-142-3p, let-7f, miR-550, miR-759, miR-573, miR-150, miR-214, miR-637, let7c, miR-381, miR-27a, and miR-575. It is further contemplated that other molecules described herein as dowregulated can similarly be used in treatment, diagnosis or screening methods. Such treatment may comprise the administration nucleic acid molecules to supplement the lack of said miRNAs or inducer of the expression of said miRNAs.

The term "immunologic disorder" refers to a disorder involving cells of the immune system, for example lymphocytes. Such immunologic disorders include disorders associated with the inflammatory process for example. The immunologic disorder is not limited to an immunologic cell proliferative disorder.

The term "inflammation" refers to the local accumulation of fluid, plasma proteins, and white blood cells initiated by physical injury, infection or a local immune response. Inflammatory disorders or diseases are diseases characterized by abnormalities of the inflammation process. Thus, representative examples of diseases or disorders associated with an inflammation, and are therefore screenable by the methods of the present invention (as well as screening candidate therapeutic agents for modulation of inflammation or response associated with miRNA expression levels) of the present inventioninclude, for example, idiopathic inflammatory diseases or disorders, chronic inflammatory diseases or disorders, acute inflammatory diseases or disorders, autoimmune diseases or disorders, infectious diseases or disorders, inflammatory malignant diseases or disorders, inflammatory transplantation-related diseases or disorders, inflammatory degenerative diseases or disorders, diseases or disorders associated with a hypersensitivity, inflammatory cardiovascular diseases or disorders, inflammatory cerebrovascular diseases or disorders, peripheral vascular diseases or disorders, inflammatory glandular diseases or disorders, inflammatory gastrointestinal diseases or disorders, inflammatory cutaneous diseases or disorders, inflammatory hepatic diseases or disorders, inflammatory neurological diseases or disorders, inflammatory musculo-skeletal diseases or disorders, inflammatory renal diseases or disorders, inflammatory reproductive diseases or disorders, inflammatory systemic diseases or disorders, inflammatory connective tissue diseases or disorders, inflammatory tumors, necrosis, inflammatory implant-related diseases or disorders, inflammatory aging processes, immunodeficiency diseases or disorders, proliferative diseases and disorders and inflammatory pulmonary diseases or disorders, as is detailed hereinbelow.

Non-limiting examples of hypersensitivities include Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

Non-limiting examples of inflammatory cardiovascular disease or disorder include occlusive diseases or disorders, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

Stenosis is an occlusive disease of the vasculature, commonly caused by atheromatous plaque and enhanced platelet activity, most critically affecting the coronary vasculature.

Restenosis is the progressive re-occlusion often following reduction of occlusions in stenotic vasculature. In cases where patency of the vasculature requires the mechanical support of a stent, in-stent-stenosis may occur, re-occluding the treated vessel.

Non-limiting examples of cerebrovascular diseases or disorders include stroke, cerebrovascular inflammation, cerebral hemorrhage and vertebral arterial insufficiency.

Non-limiting examples of peripheral vascular diseases or disorders include gangrene, diabetic vasculopathy, ischemic bowel disease, thrombosis, diabetic retinopathy and diabetic nephropathy.

Non-limiting examples of autoimmune diseases or disorders include all of the diseases caused by an immune response such as an autoantibody or cell-mediated immunity to an autoantigen and the like. Representative examples are chronic rheumatoid arthritis, juvenile rheumatoid arthritis, systemic lupus erythematosus, scleroderma, mixed connective tissue disease, polyarteritis nodosa, polymyositis/dermatomyositis, Sjogren's syndrome, Bechet's disease, multiple sclerosis, autoimmune diabetes, Hashimoto's disease, psoriasis, primary myxedema, pernicious anemia, myasthenia gravis, chronic active hepatitis, autoimmune hemolytic anemia, idiopathic thrombocytopenic purpura, uveitis, vasculitides and heparin induced thrombocytopenia.

Non-limiting examples of inflammatory glandular diseases or disorders include pancreatic diseases or disorders, Type I diabetes, thyroid diseases or disorders, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome.

Non-limiting examples of inflammatory gastrointestinal diseases or disorders disorders include colitis, ileitis, Crohn's disease, chronic inflammatory intestinal disease, inflammatory bowel syndrome, chronic inflammatory bowel disease, celiac disease, ulcerative colitis, an ulcer, a skin ulcer, a bed sore, a gastric ulcer, a peptic ulcer, a buccal ulcer, a nasopharyngeal ulcer, an esophageal ulcer, a duodenal ulcer and a gastrointestinal ulcer.

Non-limiting examples of inflammatory cutaneous diseases or disorders disorders include acne, and an autoimmune bullous skin disease.

Non-limiting examples of inflammatory hepatic diseases or disorders include autoimmune hepatitis, hepatic cirrhosis, and biliary cirrhosis.

Non-limiting examples of inflammatory neurological diseases or disorders include multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease or disorder, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, Huntington's disease, AIDS associated dementia, amyotrophic lateral sclerosis (AML), multiple sclerosis, stroke, an inflammatory retinal disease or disorder, an inflammatory ocular disease or disorder, optic neuritis, spongiform encephalopathy, migraine, headache, cluster headache, and stiff-man syndrome.

Non-limiting examples of inflammatory connective tissue diseases or disorders include autoimmune myositis, primary Sjogren's syndrome, smooth muscle autoimmune disease or disorder, myositis, tendinitis, a ligament inflammation, chondritis, a joint inflammation, a synovial inflammation, carpal tunnel syndrome, arthritis, rheumatoid arthritis, osteoarthritis, ankylosing spondylitis, a skeletal inflammation, an autoimmune ear disease or disorder, and an autoimmune disease or disorder of the inner ear.

Non-limiting examples of inflammatory renal diseases or disorders include autoimmune interstitial nephritis and/or renal cancer.

Non-limiting examples of inflammatory reproductive diseases or disorders include repeated fetal loss, ovarian cyst, or a menstruation associated disease or disorder.

Non-limiting examples of inflammatory systemic diseases or disorders include systemic lupus erythematosus, systemic sclerosis, septic shock, toxic shock syndrome, and cachexia.

Non-limiting examples of infectious disease or disorder include chronic infectious diseases or disorders, a subacute infectious disease or disorder, an acute infectious disease or disorder, a viral disease or disorder, a bacterial disease or disorder, a protozoan disease or disorder, a parasitic disease or disorder, a fungal disease or disorder, a mycoplasma disease or disorder, gangrene, sepsis, a prion disease or disorder, influenza, tuberculosis, malaria, acquired immunodeficiency syndrome, and severe acute respiratory syndrome.

Non-limiting examples of inflammatory transplantation-related diseases or disorders include graft rejection, chronic graft rejection, subacute graft rejection, acute graft rejection hyperacute graft rejection, and graft versus host disease or disorder. Exemplary implants include a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, and a respirator tube.

Non-limiting examples of inflammatory tumors include a malignant tumor, a benign tumor, a solid tumor, a metastatic tumor and a non-solid tumor.

Non-limiting examples of inflammatory pulmonary diseases or disorders include asthma, allergic asthma, emphysema, chronic obstructive pulmonary disease or disorder, sarcoidosis and bronchitis.

An example of a cell proliferative disease or disorder is cancer.

Inflammatory Disease

The present invention provides methods for the diagnosis (through miRNA biomarker screening), screening of candidate therapeutic agents (e.g. by measuring the effect of the therapeutic agent on the observed upregulation or down-regulation of miRNA expression levels associated with a disease condition), treatment of any type of inflammatory disorder or inflammatory disease. Inflammatory disorders are disorders in which an excessive or unregulated inflammatory response leads to excessive inflammatory symptoms, including signs of pain, heat, redness, swelling, host tissue damage, and loss of tissue function. The present invention is of particular use in patients with signs and symptoms of inflammatory disease associated with a specific condition. The present invention is further of particular use in screening for triggers of an inflammatory disease or condition.

Inflammatory disorders may be acute or chronic. Chronic inflammatory disorders are disorders in which an excessive or unregulated inflammatory response prolongs for weeks, months, years, or indefinitely. Chronic inflammatory disorders include chronic inflammatory disorders of the airways, bowel, connective tissues, joints, and skin.

Chronic inflammatory airway disorders that may be treated using the present invention include, for example, asthma (e.g., allergic asthma, non-allergic/intrinsic asthma, exercise-induced asthma, nocturnal asthma, occupational asthma, and steroid resistant asthma), exercise-induced bronchospasm (EIB), and chronic obstructive pulmonary disease (COPD).

Chronic inflammatory bowel diseases (IBD) that may addressed/screened/treated treated using the present invention include, for example, ulcerative colitis, and Crohn's disease.

Chronic inflammatory connective tissue diseases that may be addressed/screened/treated using the present invention include, for example, lupus erythematosus, scleroderma, Sjogren's syndrome, poly- and dermatomyositis, vasculitis, and MCTD.

Chronic inflammatory joint diseases that may be screened or treated using the present invention include, for example, rheumatoid arthritis (e.g., polyarthritis), juvenile chronic arthritis (Still's disease), rheumatoid spondylitis, lupus erythematosus, ankylosing spondylitis, psoriatic arthritis, and reactive arthritis. One aspect of the present invention provides novel regimens for treating chronic inflammatory joint diseases of the hip, including rheumatoid arthritis of the hip, bursitis of the hip, and osteoarthritis of the hip.

Chronic inflammatory skin diseases that may be screened or treated using the present invention include, for example, psoriasis, diskoid lupus erythematosus, scleroderma, hives, rosacea, dermatitis, and atopic dermatitis (eczema).

The present invention is of particular use in patients with other diseases associated with inflammation, including, for example, spondyloarthropies, cardiomyopathy, atherosclerosis vasculitis (e.g., anti-neutrophil cytoplasmic Ab (ANCA)-associated vasculitis including chronic and relapsing ANCA-associated vasculitis), acute renal disease, chronic renal disease, glomerulonephritis, inflammatory eye disorders (e.g., retinitis), tuberculosis, chronic cholecystitis, bronchiectasis, Hashimoto's thyroidiitis, Silicosis and other pneumoconioses, and hyper-IgG4 disease.

The present invention is also useful in the screening or treatment of inflammatory side effects associated with a pharmaceutical agent, wherein the inflammation is not associated with the pharmaceutical agent's desired effect.

Immune System Disease

The present invention is of particular use in patients with immunologic disease, including clinical problems associated with an inappropriate immune response.

Immunologic diseases that may be treated using the present invention include autoimmunity, transplant rejection, graft rejection, graft-versus-host disease, and hypersensitivity.

Autoimmunity is a tissue damaging immune response directed specifically and inappropriately against one or more self antigens. Autoimmune diseases that may benefit from treatment using the present invention include, for example, acute renal disease, chronic renal disease, pemphigus vulgaris, acute anti-neutrophil cytoplasmic Ab (ANCA)-associated vasculitis, acute disseminated encephalomyelitis (ADEM), Addison's disease, ankylosing spondylitis, antiphospholipid Ab syndrome (APS), aplastic anemia, autoimmune hepatitis, autoimmune oophoritis, coeliac disease, Crohn's disease, diabetes mellitus type I, goodpastures's syndrome, Grave's disease, Lupus erythematosus (e.g., systemic lupus erythematosus (SLE), lupus nephritis, and lupus cerebritis), and multiple sclerosis.

Hypersensitivity reactions or allergies are exaggerated, inappropriate, or prolonged immune responses that cause damage to otherwise normal tissue. Allergies that may benefit from treatment with the present invention include, for example, allergic rhinitis (hay fever), atopic dermatitis (eczema), allergic conjunctivitis, eosinophilic granuloma, septic shock, adult respiratory distress syndrome (ADSS), endotoxic shock, and respiratory distress syndrome.

An aspect of the present invention regards the detection, classification, prevention, diagnosis, prognosis and treatment of cancer, especially lung cancers and breast cancer.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as nonpathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal cell carcinoma, prostate cancer and/or testicular tumours, non-small cell carcinoma of the lung, cancer of the small intestine and cancer of the esophagus.

It is an object of the present invention to provide a method to detect, classify, diagnose and enable a prognosis of cancer. Preferably it is an object of the present invention to provide a method to detect, classify, diagnose and enable a prognosis of lung cancer or breast cancer. The breast cancer may be any breast cancer, specifically any breast cancer selected from the group of: luminal A, luminal B, HER2-overexpressing, basal and normal-like subtypes of breast cancer.

An embodiment of the present invention regards lung cancer. Lung cancer is the malignant transformation and expansion of lung tissue, and is the most lethal of all cancers worldwide, responsible for 1.2 million deaths annually. It is caused predominantly by cigarette smoking, and predominantly affected men, but with increased smoking among women, it is now the leading cause of death due to cancer in women. However, some people who have never smoked still get lung cancer.

It is an object of the present invention to provide a method to detect, classify, diagnose and enable a prognosis of cancer. Preferably it is an object of the present invention to provide a method to detect, classify, diagnose and enable a prognosis of lung cancer. The lung cancer may be any lung cancer, specifically any lung cancer selected from the group of small cell lung cancer (SCLC) and non-small cell lung cancer (NSCLC).

EXAMPLE 1

Material and Methods

MiRNA oligonucleotide synthesis: About 800 miRNAs miRNA mature sequences were obtained from miRBase (http://microrna.sanger.ac.uk/), converted to complementary DNA sequence and triplicate the sequences, then chemically synthesized (also include several positive controls (tRNA) and negative controls) at IDT (Integrated DNA Technologies, Inc.) at 25 nmole scale and diluted at 100 μm in 384-well plate format.

Preparation of miRNA oligo Dot-blot nylon membrane array: GeneScreen Plus Hybridization Transfer Membrane are cut to the size of 95 mm×120 mm. Dilute Oligo in TE to 50 μM in a 384 well plates using multiple channel pipetor. Add equal volume of 2× Denature buffer (0.5 N NaOH, 1.0 M NaCl) to the diluted oligos, mix well and denature DNA for 10 minutes at room temperature. Add equal volume of dilution Buffer (0.1×SSC, 0.125 N NaOH). Use a 384-pin plate replicator (V&P Scientific) to duplicately spot the miRNA library onto the membranes. Put the membrane into a tray that containing 500 mlo of washing buffer (0.5 N NaCl, 0.5 M Tris-HCl, pH 7.5) to neutralize and wash the membrane. Remove the membrane and place the wet membrane on a piece of wet filter paper. This will prevent the membrane from drying. Fix the DNA to the membrane by UV Autocrosslinking (1200 uJoulex100, Stratalinker® 2400 UV Crosslinker, 120V).

MiRNA extraction: Total RNA is isolated by standard Trizol (guanidinium isothiocyanate/acidic phenol) method according to manufacturer's instructions.

RNA labeling: 10 μg of total RNA will be enzymaticaly radiolabeled by poly (A) polymerase. For two samples of labeling, mix the following: 10 μl of 5× Poly(A) Polymerase Reaction Buffer; 10 μg total RNA; 50 μCi$^{32}$P-α—ATP; 1 μl of Yeast Poly(A) Polymerase (USB) and 1 μl of RNasin. Incubate at 37° C. for about 2 to 3 hours.

Hybridization: Prehybridized in 3 ml MicroHyb Hybridization Buffer (Invitrogen) in a hybridization tube at 40° C. for at least 30 min, then followed by an overnight hybridization in new hybridization buffer containing the P$^{32}$ labeled RNA probe. Following hybridization membranes were washed twice with 20 ml of 2×SSC/0.5% SDS at 37° C. The second wash was performed once in 20 ml of 1×SSC/0.5% SDS at 37° C. Each for 10 min. Finally, the spot signals on the membrane were scanned using the GE Typhon Phosphoimage system and quantified using Image Quant software (Molecular Dynamics). After exposure the membranes were stripped with 0.2% SDS at 72° C. for 15 min twice.

EXAMPLE 2 miRNAs are Downregulated in Inflamed Lungs

Asthma is a chronic inflammatory lung disease that results in partially reversible constriction of the airways. To examine whether miRNAs are involved in this process, we first established chronic asthma models using Ova (ovalbumin) as antigen stimulation. The successful establishment of the chronic asthma model was confirmed by AHR (airway hyperreactivity) measurements (FIG. 1).

Figure 2:
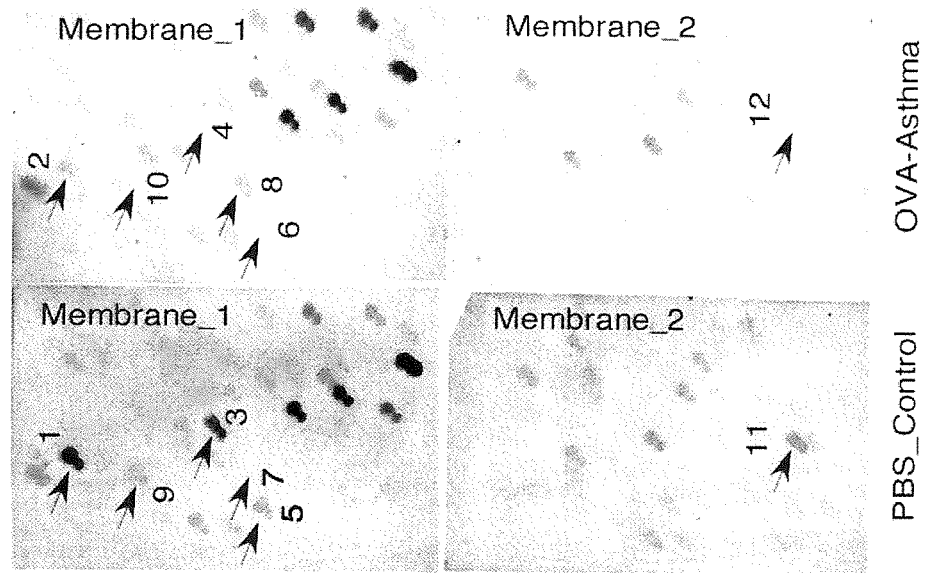
FIG. 2 is a dot-blot miRNA array.
Figure 3:
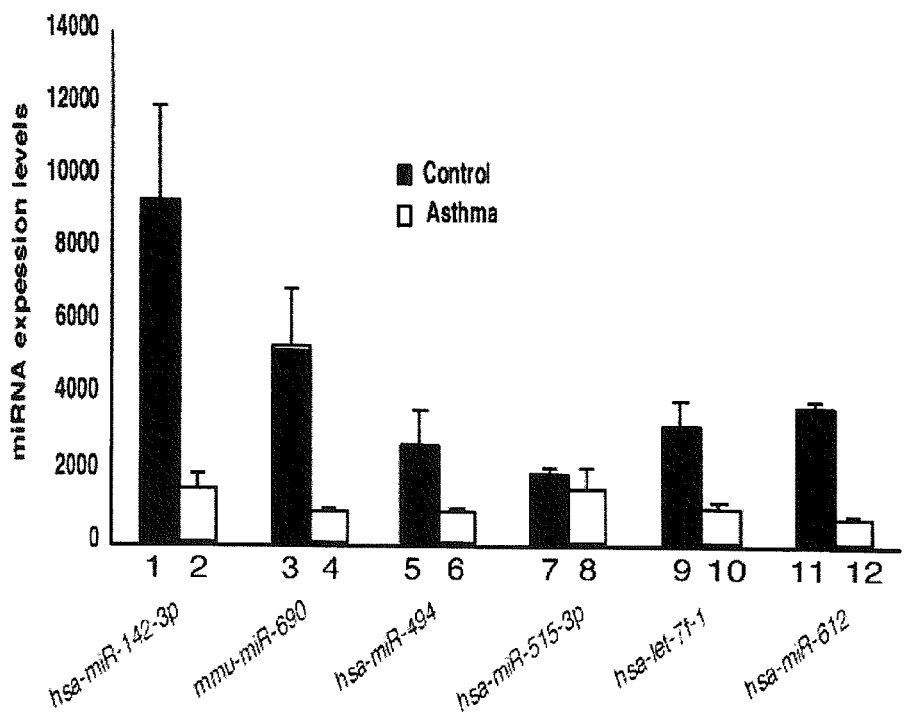
FIG. 3 is a bar graph comparison of selected miRNA expression levels from the dot-blot miRNA array of FIG. 2.

MiRNA profiling of chronic asthma mouse model was performed. FIGS. 1 through 3 shows the results. Six female BALB/c mice were primed by i.p. injection of 50 μg of OVA in PBS plus 100 μl of alum (200-μl total volume per mouse) on days 0, 7 and 14. Six control mice were also injected i.p. with PBS plus 100 μl of alum (200-μl total volume per mouse). OVA/alum-primed (OVA) and alum-primed (control) mice were then challenged under light anesthesia (isoflurane) by intranasal (i.n.) delivery of 50 μg of OVA in PBS (50-μl total volume) on days 28 and thereafter 3 times every week for one month. AHR (airway hyperreactivity) were measured by a plethysmograph device and accompanied software (Buxco, Inc) and the average Penhs (percentage of above baseline) were presented (FIG. 1). Dot blot miRNA array was performed and the results are presented in FIG. 2. We synthesized about 800 tri-mer oligonucleotides antisense to human and mouse mature miRNAs and control oligos from some tRNAs at IDT (Integrated DNA Technologies, Inc.). The oligos were spotted in duplicate on GeneScreen Plus (NEN) membranes with a 384 pin plate replicator (V&P Scientific). 10 ug of total RNA from normal lung or asthmatic lung were enzymaticaly radiolabeled by poly (A) polymerase at 37° C. for 2 to 3 hours. The pre- and hybridization buffer is MicroHyb Hybridization Buffer (Invitrogen). Finally, the nylon membrane oligo arrays were used for hybridization with the P$^{32}$ labeled probe at 40° C. overnight. After washing three times, the spot signal intensity on the membrane was scanned and quantitated using the Typhoon™ Phosphor Imager Imaging systems (GE Healthcare Life Sciences). Arrows show the miRNAs that change dramatically in asthma and normal tissues. A probe complementary to methonine tRNA (tRNAMet) was used as a control for normalization. FIG. 3 shows a bar graph comparison of selected miRNA expression levels from FIG. 2.

Figure 4:
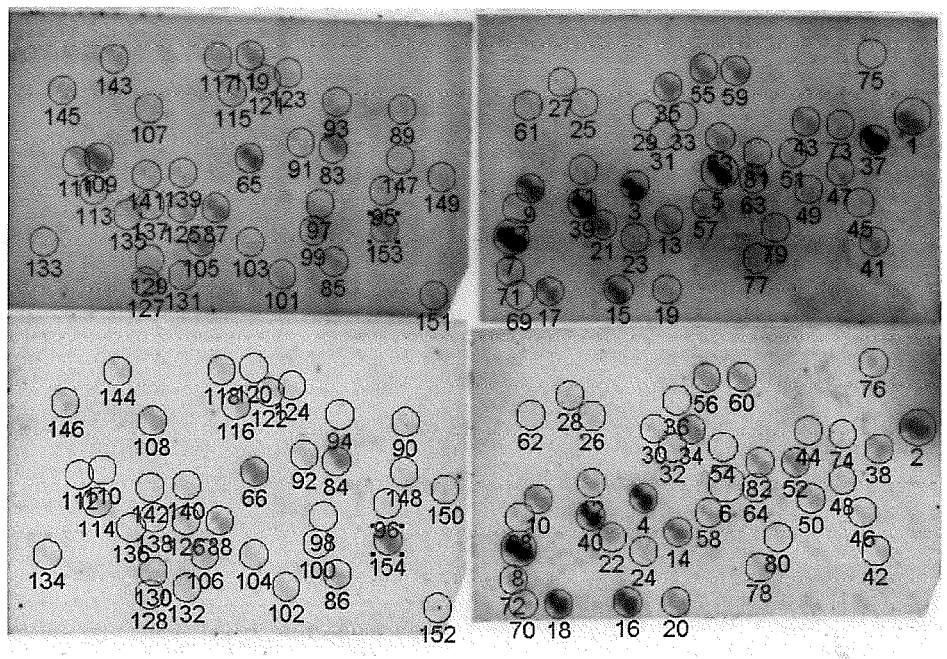
FIG. 4 is a dot-blot miRNA array. The top two dot blots are for PBS control; the bottom two dot blots are for OVA-asthma inflammation. Each individual miRNA is labeled with a number (odd numbers on the PBS control blots, even numbers on the OVA-inflammation blots) circled dot. Each even number and its previous odd number represents the same miRNA.

FIG. 4 provides a more detailed showing of the dot blot miRNA array FIG. 2. The top two dot blots are for PBS control; the bottom two dot blots are for OVA-asthma inflammation. Each individual miRNA is labeled with a number (odd numbers on the PBS control blots, even numbers on the OVA-inflammation blots) circled dot. Each even number and its previous odd number represents the same miRNA (only odd numbers are shown below): 1) hsa-miR-765; 3) mmu-miR-711; 5) mmu-miR-690; 7) mmu-miR-709; 9) mmu-miR-762; 11) mmu-miR-296; 13) mmu-miR-671; 15) mmu-miR-680; 17) mmu-miR-760; 19) mmu-miR-710; 21) mmu-miR-320; 23) mmu-miR-770-3p; 25) hsa-miR-601; 27) hsa-miR-577; 29) mmu-miR-340; 31) mmu-miR-326; 33) hsa-miR-515-3p; 35) mmu-miR-494; 37) hsa-miR-142-3p; 39) mmu-miR-705; 41) mmu-miR-674; 43) mmu-let-7f; 45) mmu-miR-466; 47) mmu-miR-540; 49) mmu-miR-702; 51) hsa-miR-584; 53) mmu-miR-505; 55) mmu-miR-17-3p; 57) mmu-miR-721; 59) hsa-miR-202; 61) hsa-miR-564; 63) mmu-miR-759; 65) hsa-miR-638; 67) mmu-miR-295; 69) mmu-miR-325; 71) mmu-miR-470; 73) hsa-miR-573; 77) mmu-miR-206; 79) mmu-miR-298; 81) mmu-miR-671; 83) hsa-miR-198; 85) mmu-miR-370; 87) mmu-miR-320; 89) hsa-miR-766; 91) hsa-miR-610; 93) mmu-let-7d; 95) mmu-let-7b; 97) mmu-let-7a; 99) mmu-miR-150; 101) hsa-miR-630; 103) mmu-miR-185; 105) hsa-miR-659; 107) hsa-miR-625; 109) mmu-miR-214; 111) hsa-miR-493-3p; 113) mmu-miR-296; 115) hsa-miR-513; 121) hsa-miR-768-5p; 123) hsa-miR-637; 125) hsa-miR-551a; 127) mmu-let-7c; 129) mmu-miR-542-5p; 131) mmu-miR-320; 133) hsa-miR-611;

135) mmu-miR-381; 137) mmu-miR-328; 139) hsa-miR-518c*; 141) mmu-miR-27a; 145) hsa-miR-608; 147) mmu-miR-30d; 149) hsa-miR-575; 151) mmu-miR-21; 153) hsa-miR-658.

FIG. 4 shows that the expression levels of some miRNAs are altered dramatically in asthma. For example, the following miRNAs, hsa-miR-142-3p, mmu-miR-690, hsa-miR-494, hsa-miR-515-3p, hsa-let-7f-1 and hsa-miR-612 have been down-regulated significantly, up to 7 folds. Interestingly, there is a global reduction of miRNA in asthma, agreeing well with the observation that there is a global repression of miRNAs in cancers. Another interesting fact is that let-7f was decreased almost to background level in asthma (numbered 43 and 44 in FIG. 4). let-7 miRNAs is frequently decreased in human lung cancers accompanied by a concomitant increase in Ras protein expression relative to normal adjacent tissue samples. Several members of the Ras proto-oncogene family, N-Ras, K-Ras and H-Ras, each contains multiple binding sites for let-7 miRNAs in their 3' UTR (untranslated regions), are conserved let-7 targets. RAS misregulation is known to be a key oncogenic event. Recent work has mapped let-7 family members to human chromosomal sites implicated in a variety of cancers, providing a mechanistic link between let-7 miRNAs and cancer. Let-7f overexpression inhibits growth of a lung cancer cell line in vitro. It is plausible that loss of miRNA control of RAS could also lead to overexpression of RAS and contribute to the conversion of normal BSCs to cancer BSCs. Taken together, the data suggests that inflammation and tumorigenesis have something in common in terms of miRNA regulation.

Figure 5:
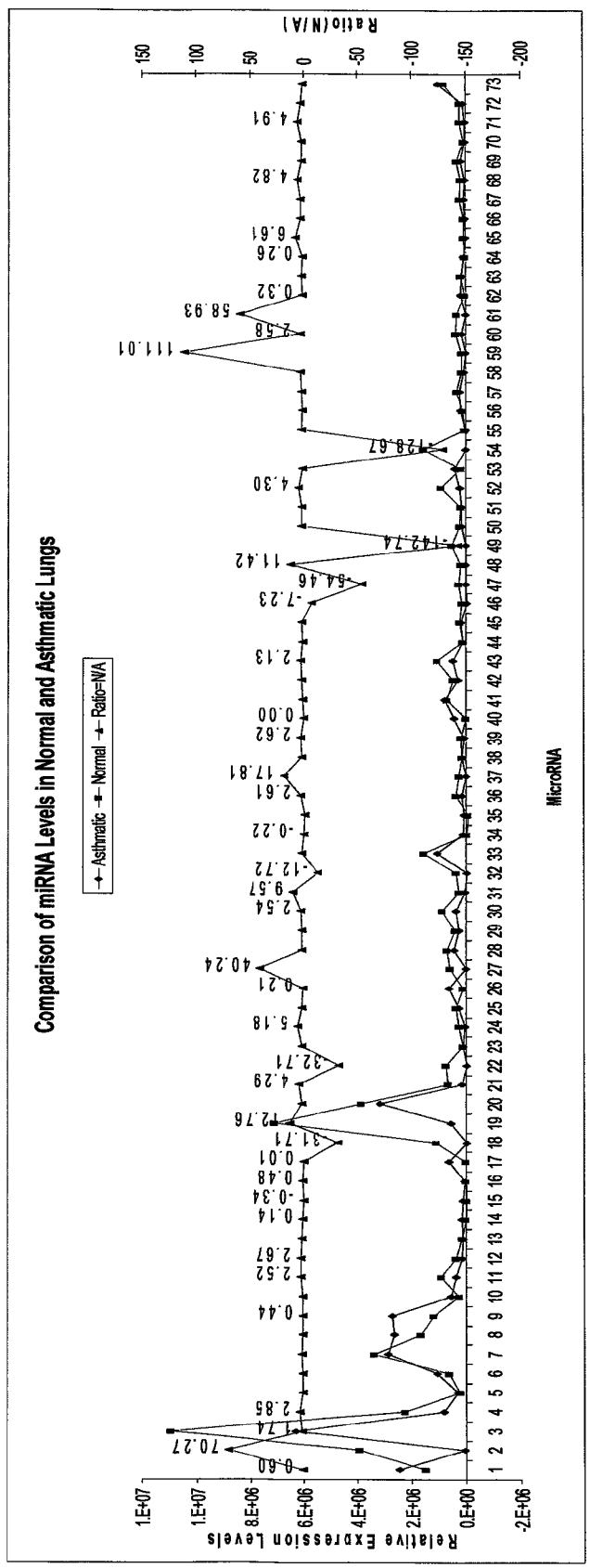
FIG. 5 is a graph showing a comparison of miRNA levels in normal and asmatic lungs.

FIG. 5 shows a comparison of miRNA expression levels in normal and asthmatic inflammation. The quantitative data were obtained from the dot blots in FIG. 4. The miRNAs are associated with the numbers along the x-axis of the graph as follows: 1. hsa-miR-765, 2. mmu-miR-711, 3. mmu-miR-690, 4. mmu-miR-709, 5. mmu-miR-762, 6. mmu-miR-296, 7. mmu-miR-671, 8. mmu-miR-680, 9. mmu-miR-760, 10. mmu-miR-710, 11. mmu-miR-320, 12. mmu-miR-770-3p, 13. hsa-miR-601, 14. hsa-miR-577, 15. mmu-miR-340, 16. mmu-miR-326, 17. hsa-miR-515-3p, 18. mmu-miR-494, 19. hsa-miR-142-3p, 20. mmu-miR-705, 21. mmu-miR-674, 22. mmu-let-7f, 23. mmu-miR-466, 24. mmu-miR-540, 25. mmu-miR-702, 26. hsa-miR-584, 27. mmu-miR-505, 28. mmu-miR-17-3p, 29. mmu-miR-721, 30. hsa-miR-202, 31. hsa-miR-564, 32. mmu-miR-759, 33. hsa-miR-638, 34. mmu-miR-295, 35. mmu-miR-325, 36. mmu-miR-470, 37. hsa-miR-573, 38. mmu-miR-206, 39. mmu-miR-298, 40. mmu-miR-671, 41. hsa-miR-198, 42. mmu-miR-370, 43. mmu-miR-320, 44. hsa-miR-766, 45. hsa-miR-610, 46. mmu-let-7d, 47. mmu-let-7b, 48. mmu-let-7a, 49. mmu-miR-150, 50. hsa-miR-630, 51. mmu-miR-185, 52. hsa-miR-659, 53. hsa-miR-625, 54. mmu-miR-214, 55. hsa-miR-493-3p, 56. mmu-miR-296, 57. hsa-miR-513, 58. hsa-miR-768-5p, 59. hsa-miR-637, 60. hsa-miR-551a, 61. mmu-let-7c, 62. mmu-miR-542-5p, 63. mmu-miR-320, 64. hsa-miR-611, 65. mmu-miR-381, 66. mmu-miR-328, 67. hsa-miR-518c*, 68. mmu-miR-27a, 69. hsa-miR-608, 70. mmu-miR-30d, 71. hsa-miR-575, 72. mmu-miR-21, 73. hsa-miR-658.

Figure 6:
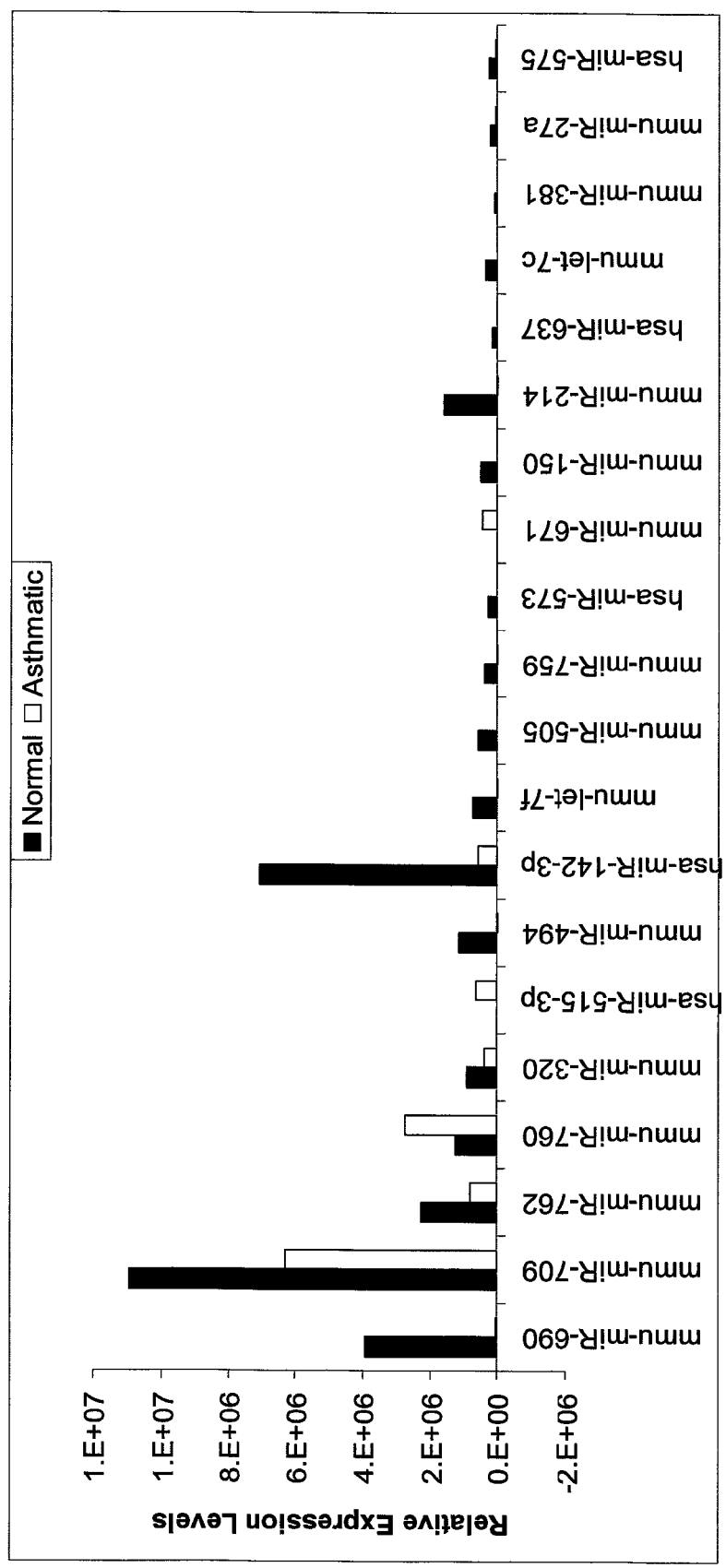
FIG. 6 is a graph showing a comparison of selected miRNA expression levels in asthma and normal control from FIG. 5.
Figure 7:
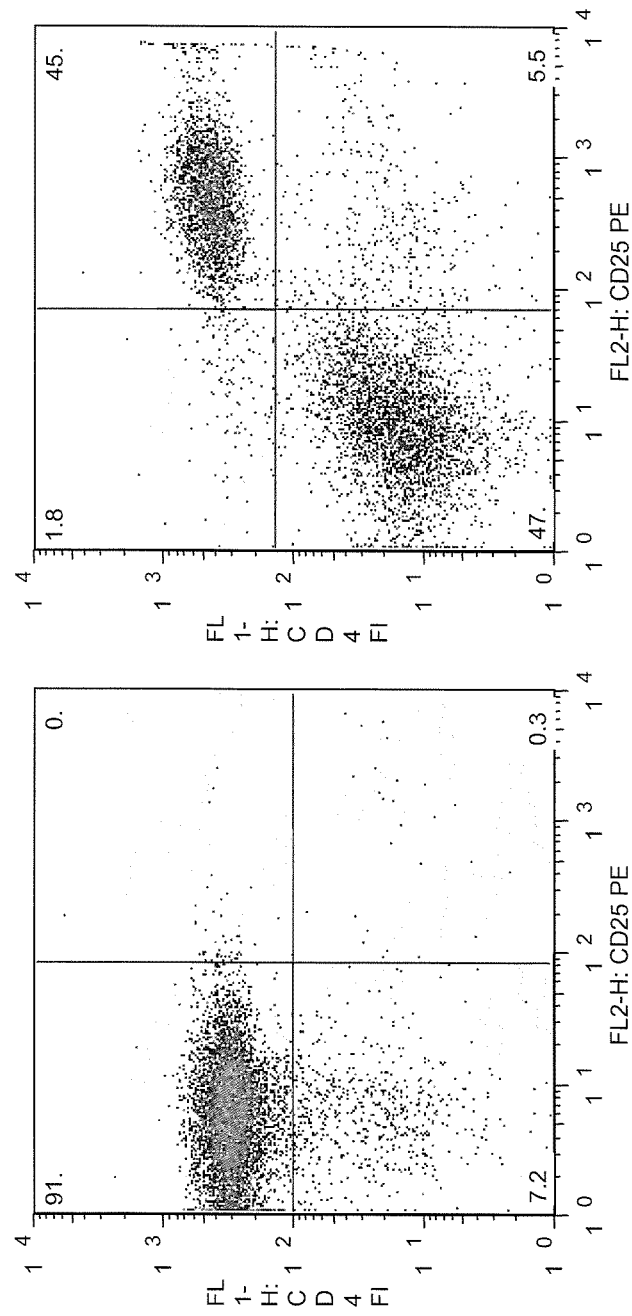
FIG. 7 is a pair of graphs.

FIG. 6 is a graph showing a comparison of selected miRNA expression levels in asthma and normal control from FIG. 5. As can be seen in the graph, a number of miRNAs are significantly down-regulated in asthmatic inflammation. These downregulated miRNAs included mmu-miR-690, mmu-miR-709, mmu-miR-762, mmu-miR-320, mmu-miR-494, hsa-miR-142-3p, mmu-let-7f, mmu-miR-505, mmu-miR-759, mmu-miR-573, and mmu-miR-214. A smaller number of miRNAs were upregulated including mmu-miR-760, has-miR-515-3p, and mmu-miR-671.

EXAMPLE 2 miRNAs are Up-Regulated in Treg

Treg cells develop in the thymus and make up 5-10% of the peripheral naïe CD4+ T lymphocyte pool in normal mice and humans. Treg cells are critical for the maintenance of peripheral self-tolerance in mice and humans. Increased numbers of CD4+CD25+ Treg cells have been found in the peripheral blood and tumor-infiltrating lymphocytes of patients with breast cancer and pancreatic cancer. To examine whether miRNAs are involved in the development and regulation of Treg, we first isolated CD4+CD25+ Treg cells from spleen of wild-type C57B mice. Total RNAs were extracted from CD4+CD25+ Treg cells and CD4+CD25− T cells (Figure A) and miRNA array assays were carried out as described above.

Figure 8:
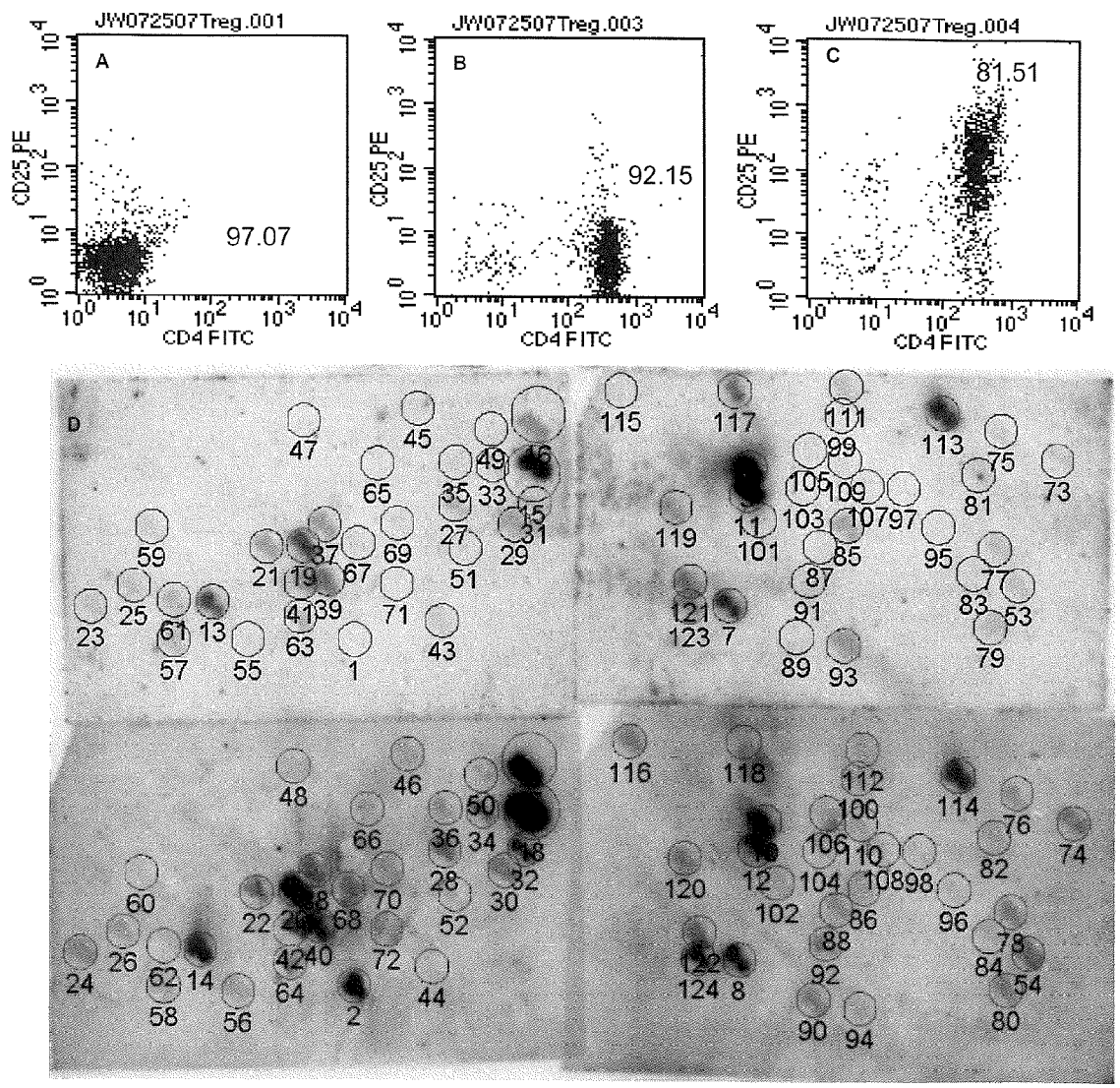
FIG. 8 is a dot-blot miRNA array.

FIG. 8 shows miRNA profiling in Treg cells. CD4+CD25+ (C) and CD4+CD25− T (B) cells were separated from the mice spleens, their RNA isolated and subjected to miRNA dot array. D. Dot blot array of Treg. The top two dot blots are for CD4+CD25− non-Treg cells; the bottom two dot blots are for CD4+CD25+ Treg cells. Each individual miRNA is labeled with a number (odd numbers on the non-Treg cells blots, even numbers on the Treg cells blots) under the circled dot. Each even number and its previous odd number represent the same miRNA (only odd numbers are shown below): 1. mmu-miR-494, 7. mmu-let-7d, 9. mmu-miR-150, 11. mmu-let-7a, 13. mmu-let-7f, 15. mmu-miR-470, 17. mmu-miR-709, 19. mmu-miR-690, 21. mmu-miR-759, 23. hsa-miR-765, 25. hsa-miR-142-3p, 27. mmu-miR-705, 29. mmu-miR-762, 31. mmu-miR-295, 33. mmu-miR-301b, 35. mmu-miR-134, 37. mmu-let-7b, 39. mmu-miR-15b, 41. mmu-miR-505, 43. hsa-miR-20a, 45. mmu-miR-680, 47. mmu-miR-23b, 49. mmu-miR-328, 51. mmu-miR-296, 53. mmu-let-7g, 55. mmu-miR-15a, 57. mmu-miR-652, 59. mmu-miR-466, 61. hsa-miR-573, 63. mmu-miR-490, 65. mmu-miR-714, 67. mmu-miR-673, 69. mmu-miR-711, 71. hsa-miR-649, 73. hsa-miR-611, 75. mmu-miR-92, 77. mmu-miR-214, 79. mmu-miR-302, 81. mmu-miR-191, 83. hsa-miR-768-3p, 85. mmu-let-7i, 87. hsa-miR-638, 89. hsa-miR-768-5p, 91. hsa-miR-588, 93. mmu-miR-422b, 95. mmu-miR-27a, 97. hsa-miR-551a, 99. hsa-miR-202*, 101. hsa-miR-363*, 103. mmu-miR-223, 105. mmu-miR-423, 107. mmu-miR-320, 109. hsa-miR-527, 111. mmu-miR-25, 113. mmu-let-7c, 115. mmu-miR-21, 117. mmu-miR-302b, 119. mmu-let-7b, 121. mmu-miR-92, 123. mmu-miR-29a.

Figure 9:
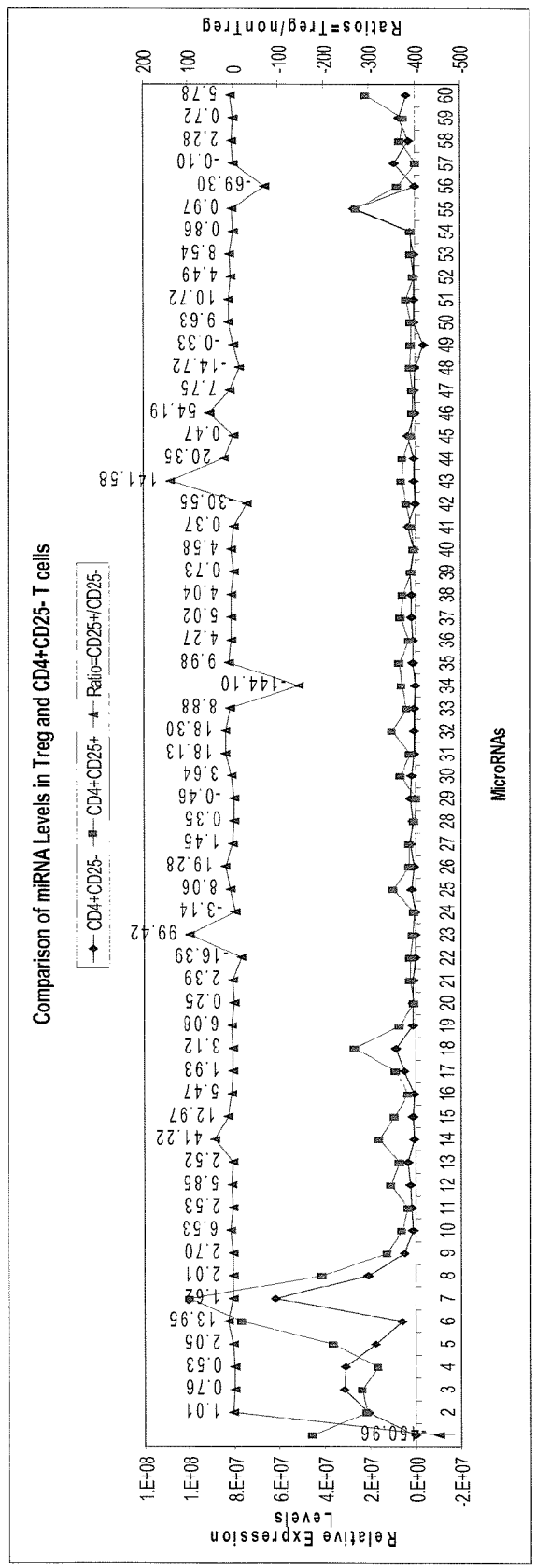
FIG. 9 is a graph showing a comparison of miRNA levels in Treg and CD4+CD25− T cells.
Figure 10:
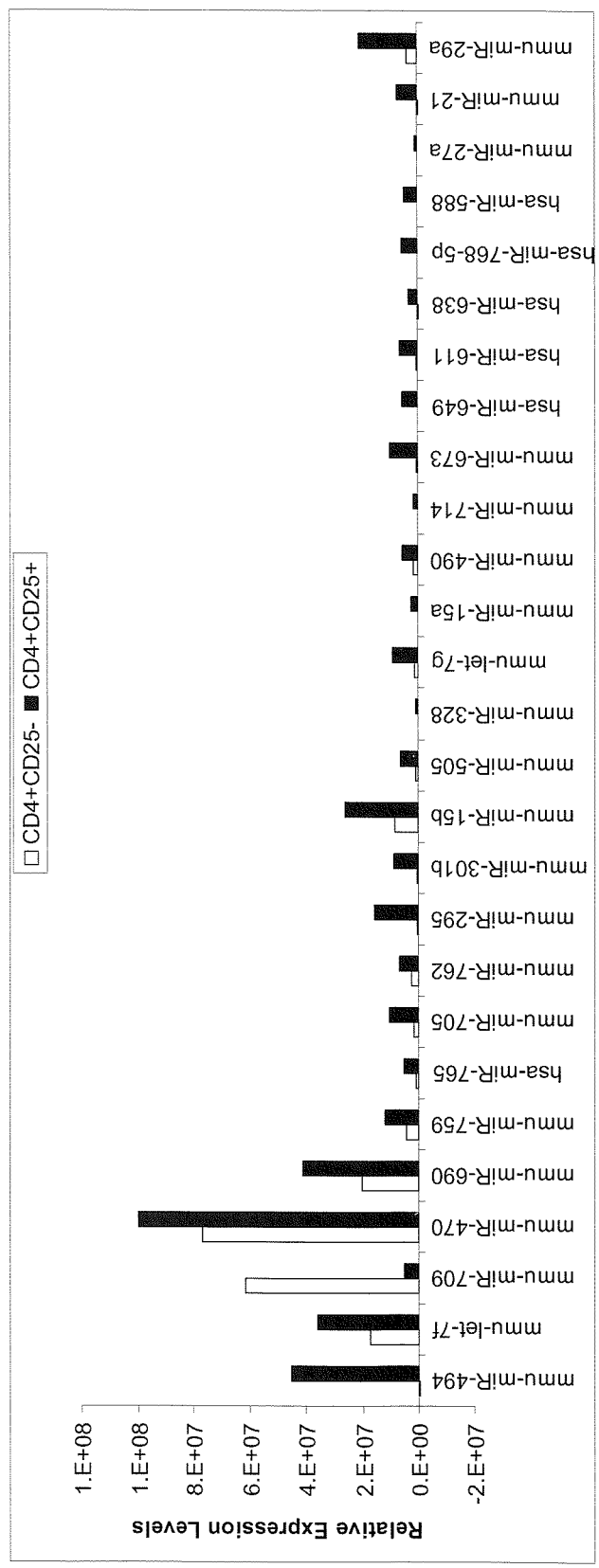
FIG. 10 is a bar graph showing a comparison of selected miRNA levels in Treg and non-Treg CD4+ cells.

FIG. 9 provides a plot showing comparison of selected miRNA expression levels from FIG. 8 comparing ratio of miRNAs from CD4+CD25+ and CD4+CD25− T cells. 1. mmu-miR-494, 2. mmu-let-7d, 3. mmu-miR-150, 4. mmu-let-7a, 5. mmu-let-7f, 6. mmu-miR-470, 7. mmu-miR-709, 8. mmu-miR-690, 9. mmu-miR-759, 10. hsa-miR-765, 11. hsa-miR-142-3p, 12. mmu-miR-705, 13. mmu-miR-762, 14. mmu-miR-295, 15. mmu-miR-301b, 16. mmu-miR-134, 17. mmu-let-7b, 18. mmu-miR-15b, 19. mmu-miR-505, 20. hsa-miR-20a, 21. mmu-miR-680, 22. mmu-miR-23b, 23. mmu-miR-328, 24. mmu-miR-296, 25. mmu-let-7g, 26. mmu-miR-15a, 27. mmu-miR-652, 28. mmu-miR-466, 29. hsa-miR-573, 30. mmu-miR-490, 31. mmu-miR-714, 32. mmu-miR-673, 33. mmu-miR-711, 34. hsa-miR-649, 35. hsa-miR-611, 36. mmu-miR-92, 37. mmu-miR-214, 38. mmu-miR-302, 39. mmu-miR-191, 40. hsa-miR-768-3p, 41. mmu-let-7i, 42. hsa-miR-638, 43. hsa-miR-768-5p, 44. hsa-miR-588, 45. mmu-miR-422b, 46. mmu-miR-27a, 47. hsa-miR-551a, 48. hsa-miR-202*, 49. hsa-miR-363*, 50. mmu-miR-223, 51. mmu-miR-423, 52. mmu-miR-320, 53. hsa-miR-527, 54. mmu-miR-25, 55. mmu-let-7c, 56. mmu-miR-21, 57. mmu-miR-302b, 58. mmu-let-7b, 59. mmu-miR-92, 60. mmu-miR-29a. FIG. 10 is a bar graph showing a comparison of selected miRNA levels in Treg and non-Treg CD4$^+$ cells.

Our data shows that the expression levels of several miRNAs are significantly changed underlying inflammation in chronic asthma mouse model. Those miRNAs include two miRNAs (let-7f and 143-3p) which are altered in lung cancer pathogenesis. Moreover, since inflammation is closely related to tumorigenesis, we hypothesize that those miRNAs are also changed at the early stage of cancer BSCs, which in turns regulates proto-oncogenes and tumor suppressor genes in BSCs allowing it to proceed to uncontrolled proliferation.

There is overall agreement that repressive complexes like miRNAs are important to maintain normal stem cell identity. On another hand, a general loss of repression, decreased expression of miRNA genes, accompanies cancer, suggesting that loss of repressive miRNAs in normal BSCs may convert normal BCSs into cancer BSCs. To test this hypothesis, we will knockdown those miRNAs that have been down-regulated in cancer BSCs and see if we can enhance the growth of normal BSCs. Conversely, we will overexpress those miRNAs in cancer BSCs, and see if we can inhibit the growth of the cancer BSCs. We have identified several miRNAs are significantly down-regulated in asthmatic lungs. From the Subaim a, we may identify several miRNA that are differentially expressed in normal and cancer BSCs. Those miRNAs may include some miRNA we identified in inflamed lungs. First we will focus on 2 to 3 miRNAs that have been known to be important to lung cancer or other cancers. i.e. let-7f.

Lung cancer has a high morbidity because it is difficult to detect early. At the earliest stage of tumorigenesis, the changes may be too subtle to be detected by conventional methods. As stated above, miRNA may serve as a fine tuner of gene regulation. In another words, miRNA profiling may be sensitive enough to detect the subtle changes at the earliest stage that convert normal stem cell to CSCs, which may aquire their specific miRNA expression patterns different from normal stem cells. The specific miRNA thus can be used as a signature of CSCs and an early marker of lung tumorigenesis.

This work allows one to identify miRNA signature for lung CSCs or early markers for lung tumorigenesis. Some will be decreased in lung. CSCs, some will be upregulated in lung CSCs, however, according to published data and our results, probably, there will be more miRNAs that are decreased in lung CSCs. Some miRNA that are significantly different in the two kinds of cells will be either knocked-down or over-expressed in these cells to further characterize their function. These expressing differently in normal and cancerous stem cells may represent as oncogenes and tumor suppressors. Our work also provides a signature for lung early tumorigenesis as well as potential targets for lung cancer interventions. The present methods can be used to determine miRNA markers for lung cancer. In addition, the miRNA markers disclosed as useful in the models of inflammation and found to be upregulated or downregulated can be used in the screening methods of lung cancer based upon the linkage discussed above between the inflammation and cancer.

In summary, miRNA are short and their number is far less than mRNA genes that they are regulating. Yet each miRNA controls about 200 mRNA genes. The miRNA regulation network serves as a fine tuner to regulate the cell machinery. Any subtle change may lead to a detectable change of miRNA expression pattern. That's why miRNA is so far the best molecular marker for different cell types and different developmental stages. Therefore, miRNA will prove a sensitive marker to distinguish CSCs from normal counterpart normal stem cells. In another words, miRNA may be used as early marker of tumorigenesis. These markers can be used for the early diagnosis of lung cancer, and potential targets for lung cancer treatments.

EXAMPLE 3

Role of MicroRNAs in the Pathogenesis of Asthma

Figure 19:
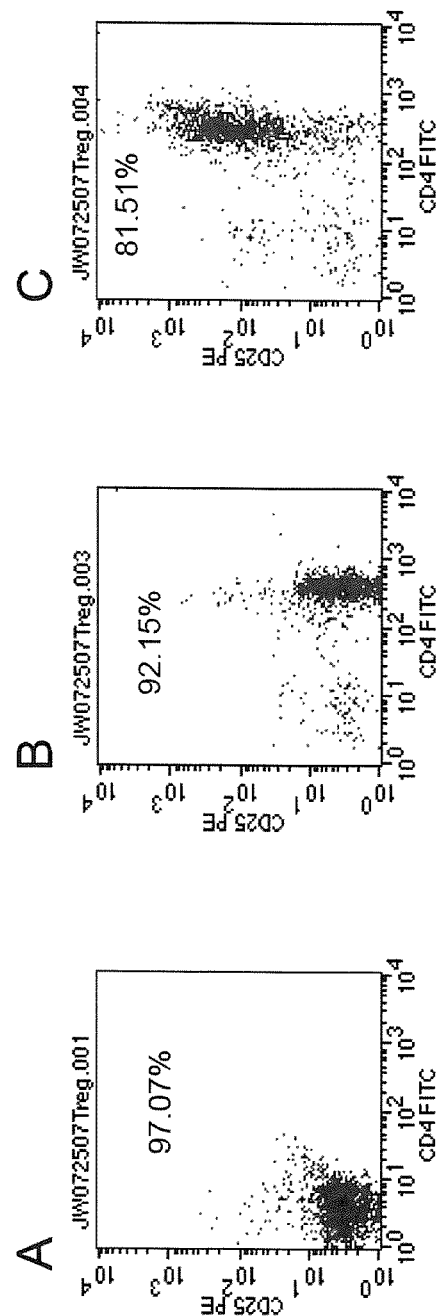
FIG. 19 shows miRNA profiling in Treg cells. CD4+CD25+.
Figure 20:
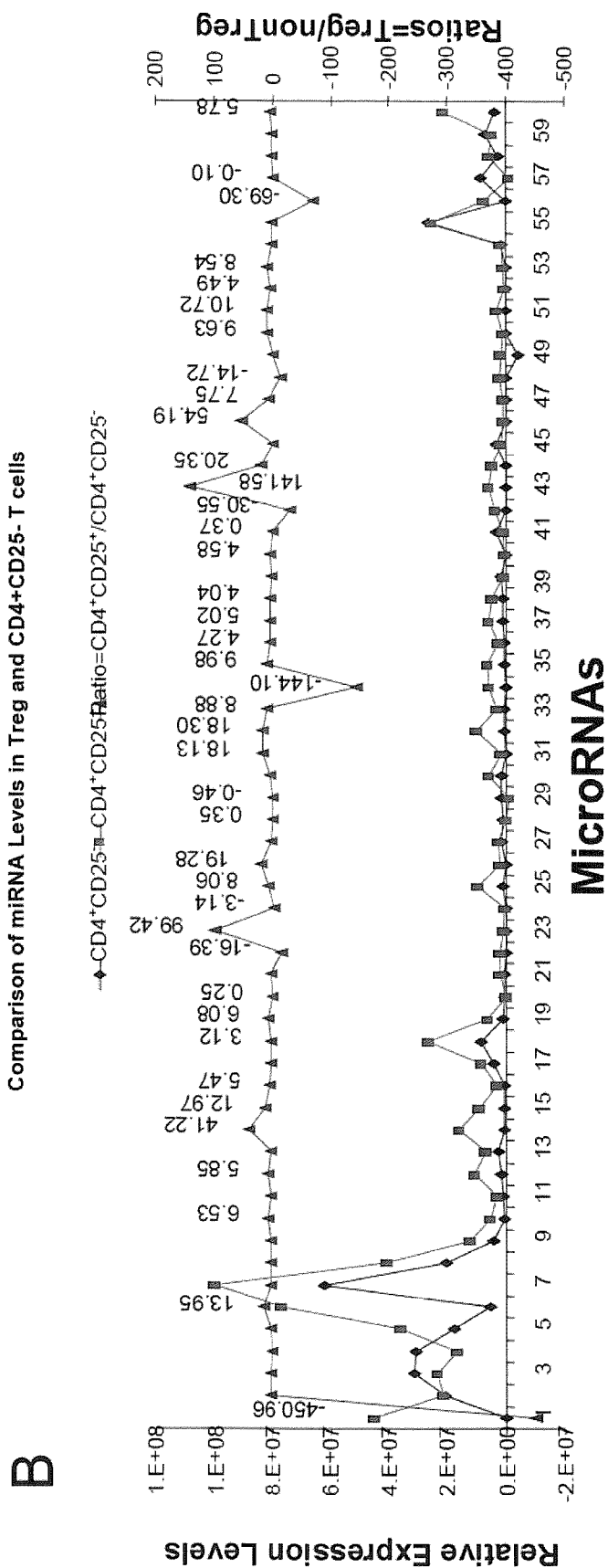
FIG. 20 is a plot showing comparison of selected miRNA expression levels from FIG. 19B comparing ratio of miRNAs from CD4+CD25+ and CD4+CD25− T cells (FIG. 20).

To investigate the role of miRNAs in the initial molecular events in the pathogenesis of asthma, we have profiled miRNA expression in (a) asthmatic mice and non-asthmatic mice (FIGS. 11-14), (b) natriuretic peptide receptor 1 (Npr1) knockout mice and wild-type mice (FIGS. 15-18), and (c) Tregs and non-Treg CD4+ T cells (FIGS. 19-20). Dot blot array and real time PCR were used in the profiling3. By comparing the miRNA profiling results from the three groups of experiments, a small group of miRNA whose levels are significantly down-regulated in asthma but up-regulated in Tregs and Npr1 KO mice was identified. These are termed as miRNA regulating asthma (miRRAs).

Figure 11:
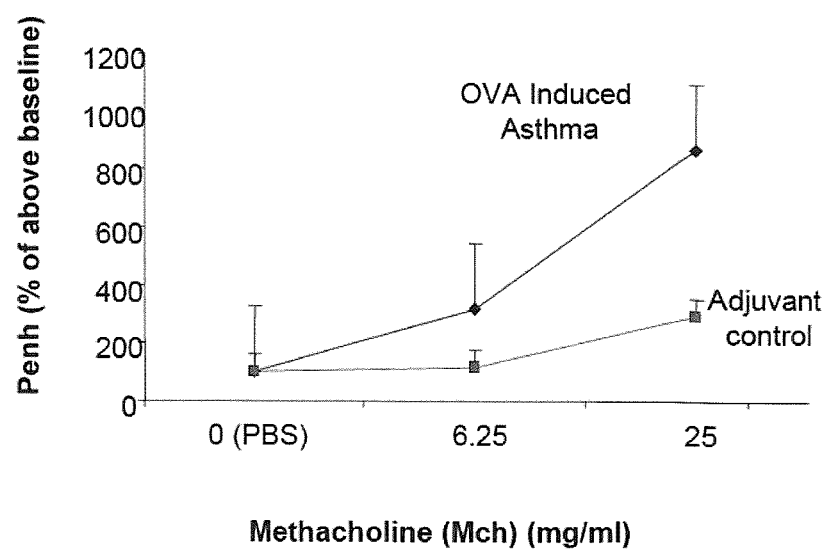
FIG. 11 is a graph showing the results of groups of female BALB/c mice (n=6) were primed by OVA/alum or alum by i.p. injection of 50 μg of VA or adjuvant on days 0 and 14 and challenged i. n. with OVA or PBS on days 28 and 29. AHR airway hyper-reactivity) was measured by Penh (enhanced pause) approach.
Figure 12:
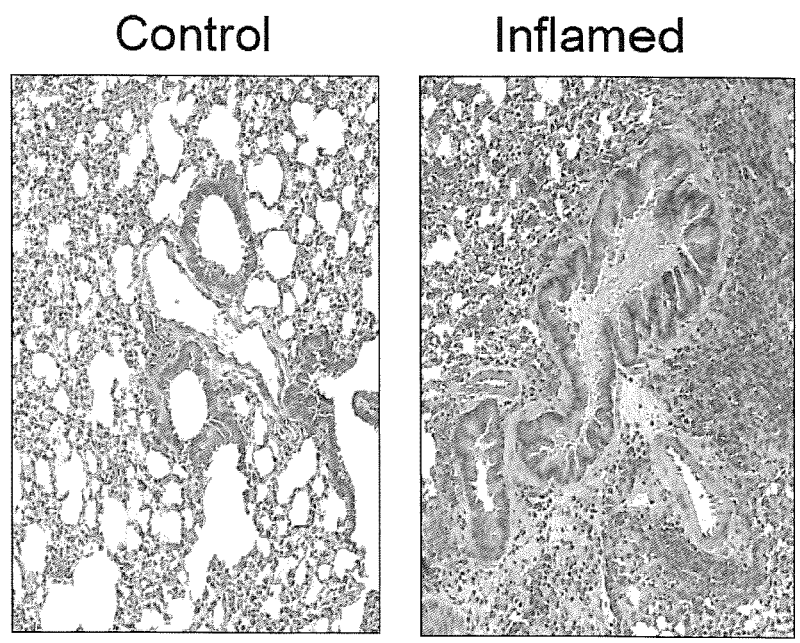
FIG. 12 shows H & E (hematoxylin, eosin) staining of lung sections, showing blockade of airway by mucus and massive infiltration of eosinophils and lymphocyte infiltration of peri-bronchial and perivenular tissue in asthmatic lung compared to that of control.
Figure 13:
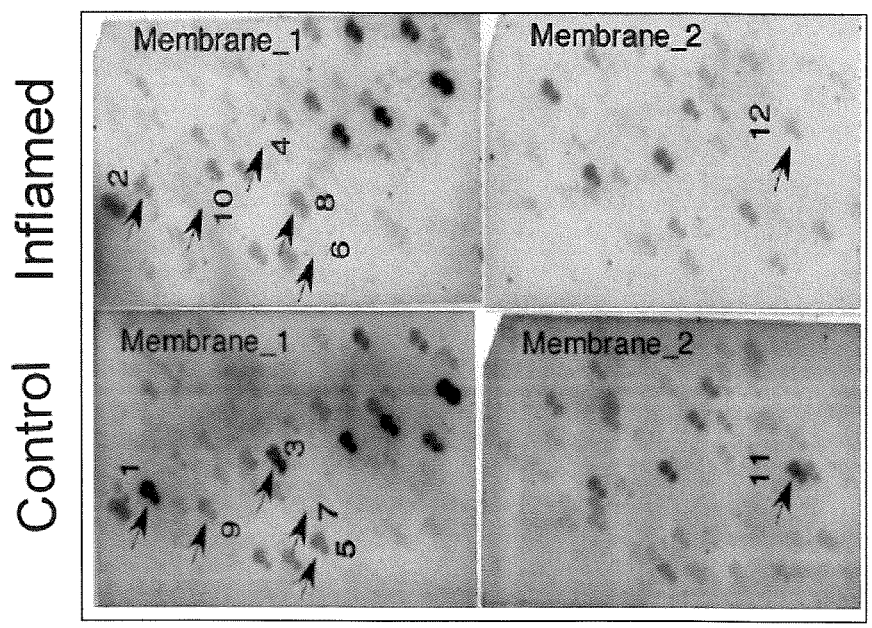
FIG. 13 is a sample dot blot miRNA array. Arrows show the miRNAs that change dramatically in inflamed and normal tissues. A probe complementary to methonine tRNA (tR-NAMet) was used as a control for normalization.
Figure 14:
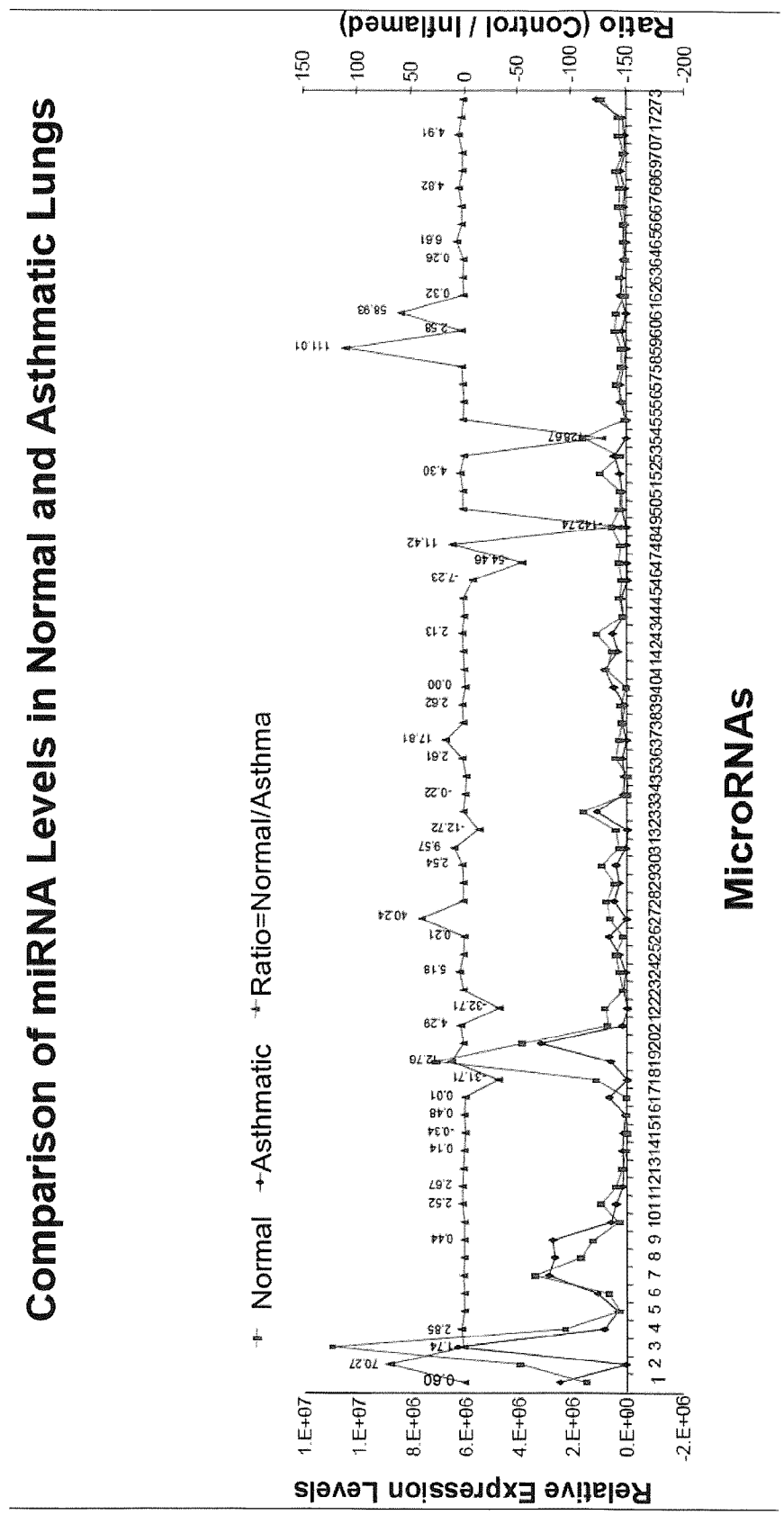
FIG. 14 is a plot showing comparison ratio of selected miRNA expression levels in normal and inflamed mice from the dot blot array (FIG. 13).
Figure 15:
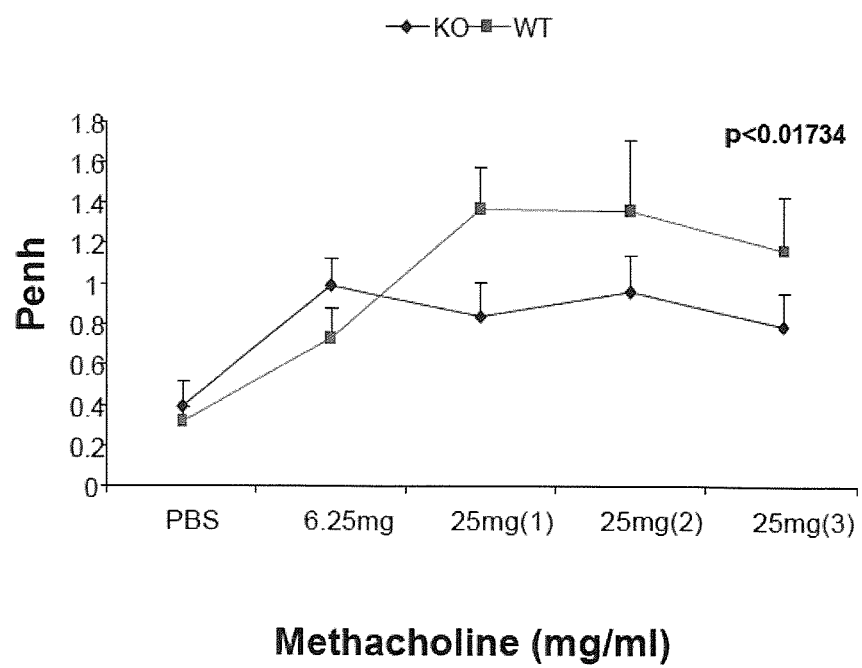
FIG. 15 is a graph showing AHR (airway hyperreactivity) as measured by Penh (enhanced pause) approach.
Figure 16:
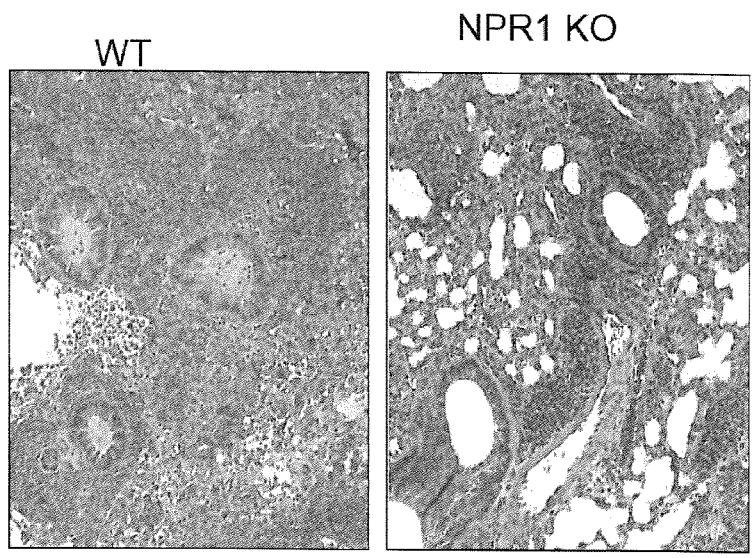
FIG. 16 shows H & E (hematoxylin, eosin) staining of lung sections, showing blockade of airway by mucus and massive infiltration of eosinophils in WT lung compared to that of KO.
Figure 17:
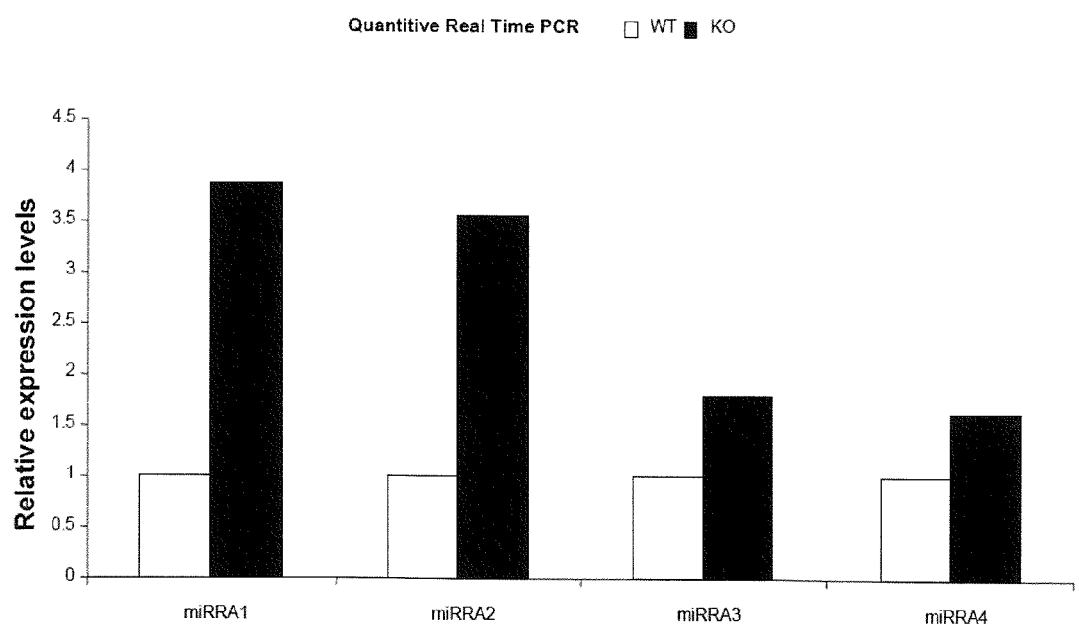
FIG. 17 is a bar graph showing expression levels of four miRNAs in WT mice relative to that of the corresponding miRNAs in KO mice. miRRA1=miR-150; miRRA2=miR-690; miRRA3=miR-515; miRRA4=miR-709; miRRA5=miR-142-3p. miRRA1=hsa-miR-150 in human and mmu-miR-150 in mouse. The sequence is UCUC-CCAACCCUUGUACCAGUG (SEQ ID NO:1).
Figure 18:
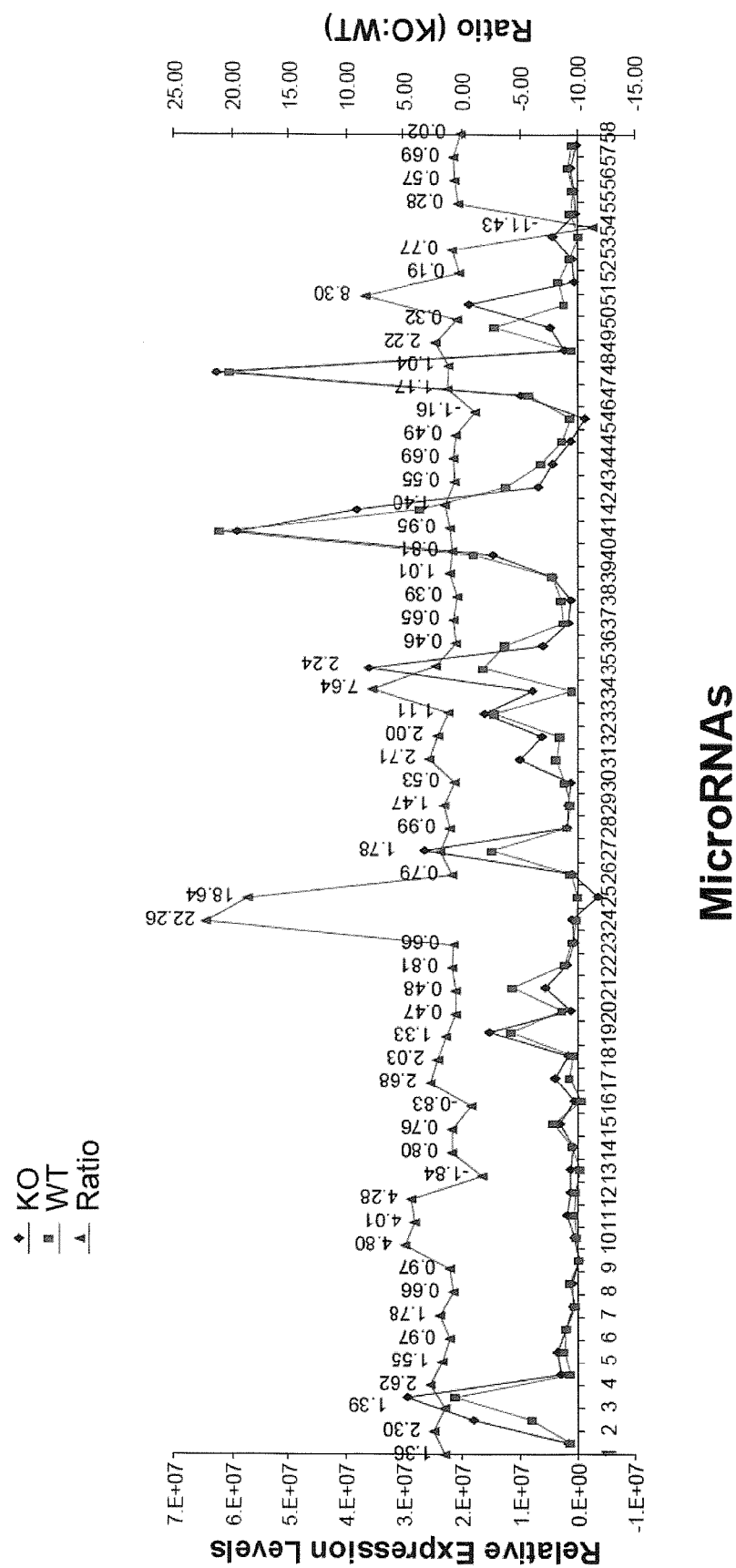
FIG. 18 is a plot showing comparison of selected miRNA expression levels comparing ratio of miRNAs from KO and WT spleen cells. Total RNAs, 10 μg, were used for miRNA dot array. Three spleens for each strain were pooled together and total RNAs prepared as described elsewhere.

FIGS. 11-14—miRNA profiling of spleens from asthmatic mice and normal mice. (FIG. 11). Groups of female BALB/c mice (n=6) were primed by OVA/alum or alum by i. p. injection of 50 μg of VA or adjuvant on days 0 and 14 and challenged i. n. with OVA or PBS on days 28 and 29. AHR airway hyper-reactivity) was measured by Penh (enhanced pause) approach. (FIG. 12). H & E (hematoxylin, eosin) staining of lung sections, showing blockade of airway by mucus and massive infiltration of eosinophils and lymphocyte infiltration of peribronchial and perivenular tissue in asthmatic lung compared to that of control. (FIG. 13). Sample dot blot miRNA array, conducted as described previously. Arrows show the miRNAs that change dramatically in inflamed and normal tissues. A probe complementary to methonine tRNA (tRNAMet) was used as a control for normalization. (FIG. 14). Plots showing comparison ratio of selected miRNA expression levels in normal and inflamed mice from the dot blot array (FIG. 13).

FIGS. 15-18—MiRNA profiling of spleens from Npr1 knockout (KO) mice and wild type (WT) C57B/6 mice. Groups of female KO mice and WT mice (n=6) were primed by OVA/alum by i. p. injection of 50 μg of OVA on days 0 and 14 and challenged i. n. with OVA on days 28 and 29. (FIG. 15) AHR (airway hyperreactivity) was measured by Penh (enhanced pause) approach. (FIG. 16) H & E (hematoxylin, eosin) staining of lung sections, showing blockade of airway by mucus and massive infiltration of eosinophils in WT lung compared to that of KO. (FIG. 17) Expression levels of four miRNAs in WT mice relative to that of the corresponding miRNAs in KO mice. (FIG. 18) Total RNAs, 10 μg, were used for miRNA dot array as described3. Three spleens for each strain were pooled together and total RNAs prepared as described elsewhere. Plots showing comparison of selected miRNA expression levels comparing ratio of miRNAs from KO and WT spleen cells.

FIGS. 19-20—miRNA profiling in Treg cells. CD4+ CD25+ (FIG. 19C) and CD4+CD25− T (FIG. 19B) cells were separated from the mice spleens, their RNA isolated and subjected to miRNA dot array as described above. Plots showing comparison of selected miRNA expression levels from B comparing ratio of miRNAs from CD4+CD25+ and CD4+CD25− T cells (FIG. 20).

Figure 21:
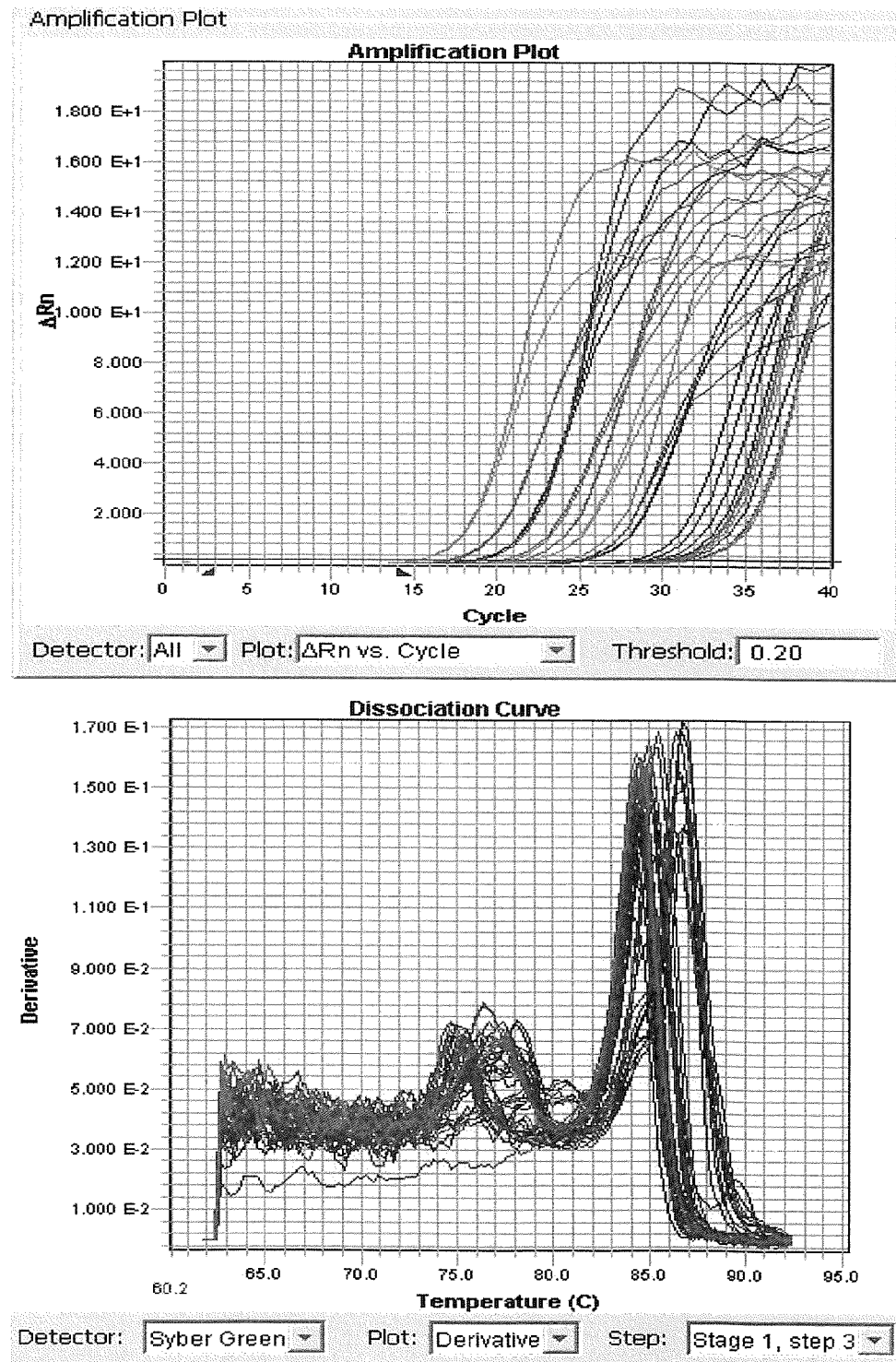
FIG. 21 shows PCR validation of the dot-blot array data. Regular RT PCR and real-time quantitative PCR (Q-PCR) C D assay for five miRNAs that are deregulated in asthma mouse model. The pooled total RNAs are prepared from four spleens each for asthmatics and controls. Q-PCRs were performed using SYBR green with the same amount of total RNA. Each primer specific to miRNA, in combination with the universal reverse primer, RTQ-U, was used for amplification.
Figure 22:
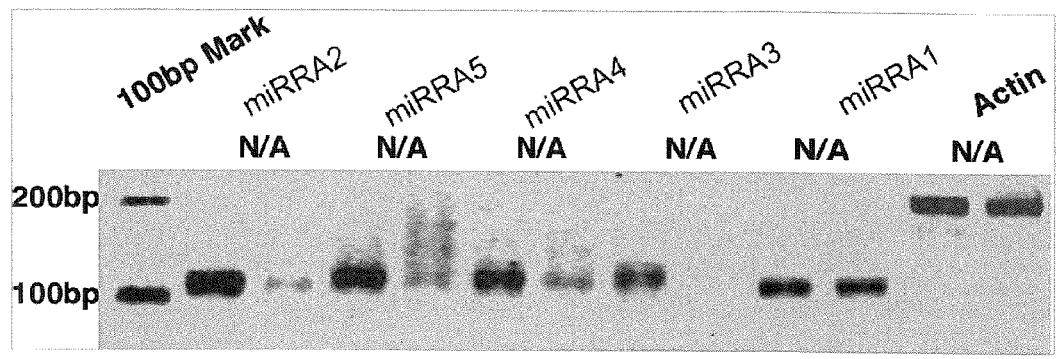
FIG. 22 shows PCR validation of the dot-blot array data.
Figure 23:
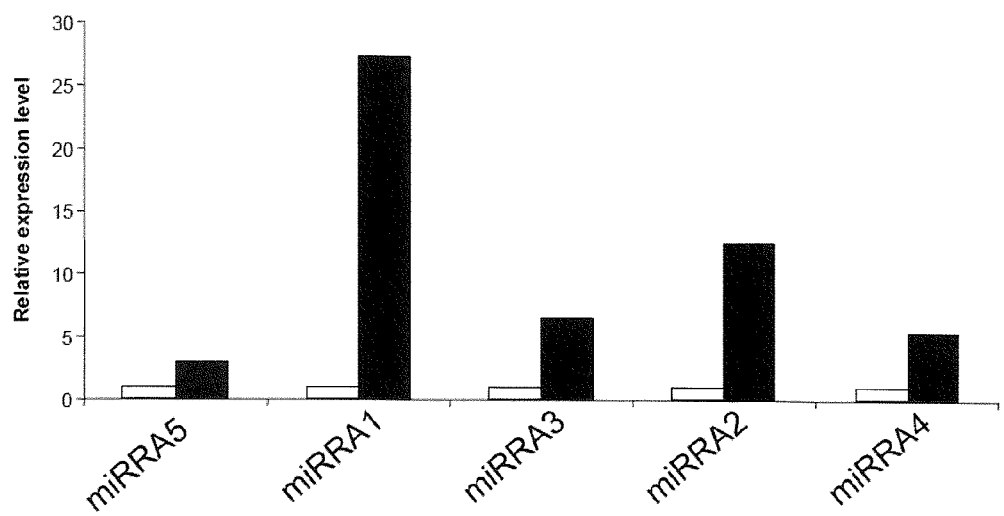
(FIG. 23) Q-PCR.

FIGS. 21-23—PCR validation of the dot-blot array data. Regular RT PCR and real-time quantitative PCR (Q-PCR) C D assay for five miRNAs that are deregulated in asthma mouse model. The pooled total RNAs are prepared from four spleens each for asthmatics and controls. Q-PCRs were performed using SYBR green with the same amount of total RNA. Each primer specific to miRNA, in combination with the universal reverse primer, RTQ-U, was used for amplification. (FIG. 21—top) Linear amplification plot of the miRNA Q-PCR assay, showing robotic exponent amplification of the miRNA replicons and sensitivity over $3 \times 10^4$ times of magnitude. The experiments were conducted in duplicate. (FIG. 21—bottom) Dissociation curves of all the miRNA amplicons, indicating specific amplification of miRNAs. (FIG. 22) & (FIG. 23) Expression levels of five miRNAs in asthmatic (OVA) relative to that of the corresponding miRNAs in control (PBS). (FIG. 22) Regular RT PCR; (FIG. 23) Q-PCR.

MicroRNAs are highly conserved in evolution from worms to humans. It is believed that most miRNAs are conserved in human and mouse in terms of sequence and function. Usually if a miRNA has same or similar sequence in human and mouse, it has same suffix (composed of miR-number) but different prefix (hsa- for human, mmu- for mouse), e.g. hsa-miR-150 and mmu-miR-150. The miRRA1 is also found in humans, and has the same sequence in mouse and human and may have the same effect in terms of gene regulation. miRRA1=miR-150; miRRA2=miR-690; miRRA3=miR-515; miRRA4=miR-709; miRRA5=miR-142-3p. miRRA1=hsa-miR-150 in human and mmu-miR-150 in mouse. The sequence is UCUCCCAACCCUUGUAC-CAGUG (SEQ ID NO:1).

Figure 24:
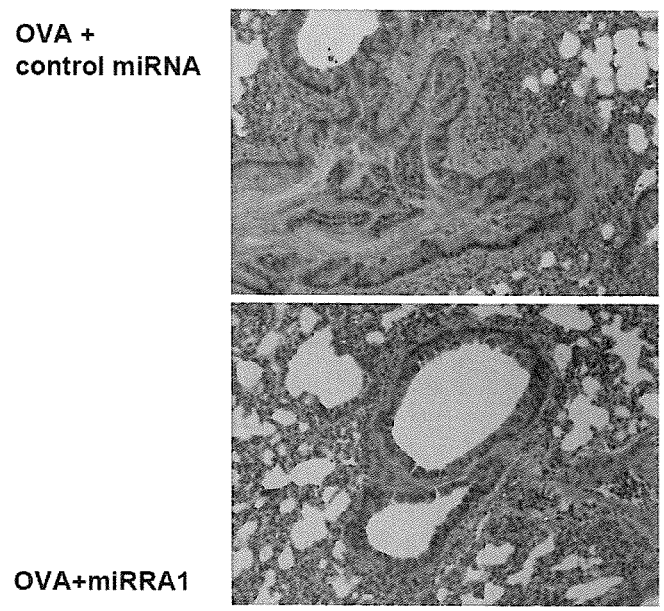
FIG. 24 shows the inhibition of OVA-induced lung inflammation by miRRA-1. 25 μg of miRRA-1 or control miRNA (scrambled) plasmid DNA were delivered i.n. into the lung of each sensitized Balb/C mouse by using nanoparticle NG042 for three consecutive days before OVA challenge. 24 hr after challenge, mice were sacrificed and half of the lung was fixed and subjected to H & E staining; another half was used for CBA cytokine assay.
Figure 25:
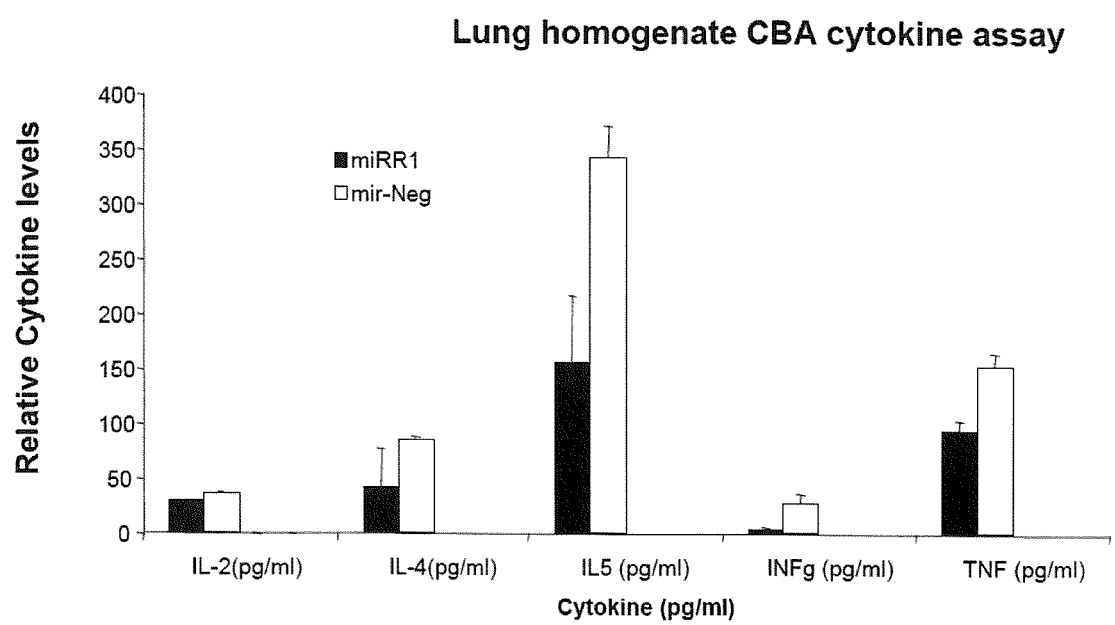
(FIG. 25) Relative Th1/Th2 cytokine levels of lung homogenates measured by CBA cytokine assay.

Because miRRAs are down-regulated in asthmatics but upregulated in Tregs and Npr1 KO mice, which have anti-inflammation properties, it is hypothesized that over-expression miRRAs may inhibit asthmatic inflammation. Indeed, we over-expressed miRRA1 in the lungs of mouse model of experimental asthma and found that miRRA1 inhibits lung inflammation and decreases both Th1 and Th2 cytokines that are involved in inflammation (FIGS. 24-25). In vitro experiments also show that miRRA1 inhibits cell proliferation and promotes apoptosis, two important processes in inflammation (FIGS. 26-30).

FIGS. 24-25—Inhibition of OVA-induced lung inflammation by miRRA-1.25 µg of miRRA-1 or control miRNA (scrambled) plasmid DNA were delivered i.n. into the lung of each sensitized Balb/C mouse by using nanoparticle NG042 for three consecutive days before OVA challenge. 24 hr after challenge, mice were sacrificed and half of the lung was fixed and subjected to H & E staining; another half was used for CBA cytokine assay. (FIG. 24) Lung histological features of mice that were sensitized, then treated with vehicle control (n=4) (top), or miRRA-1 (n=4) (bottom) before challenged with OVA (n=4). The infiltrates in the bronchovascular bundles of these animals are illustrated. Original magnification, ×100. (FIG. 25) Relative Th1/Th2 cytokine levels of lung homogenates measured by CBA cytokine assay.

Figure 26:
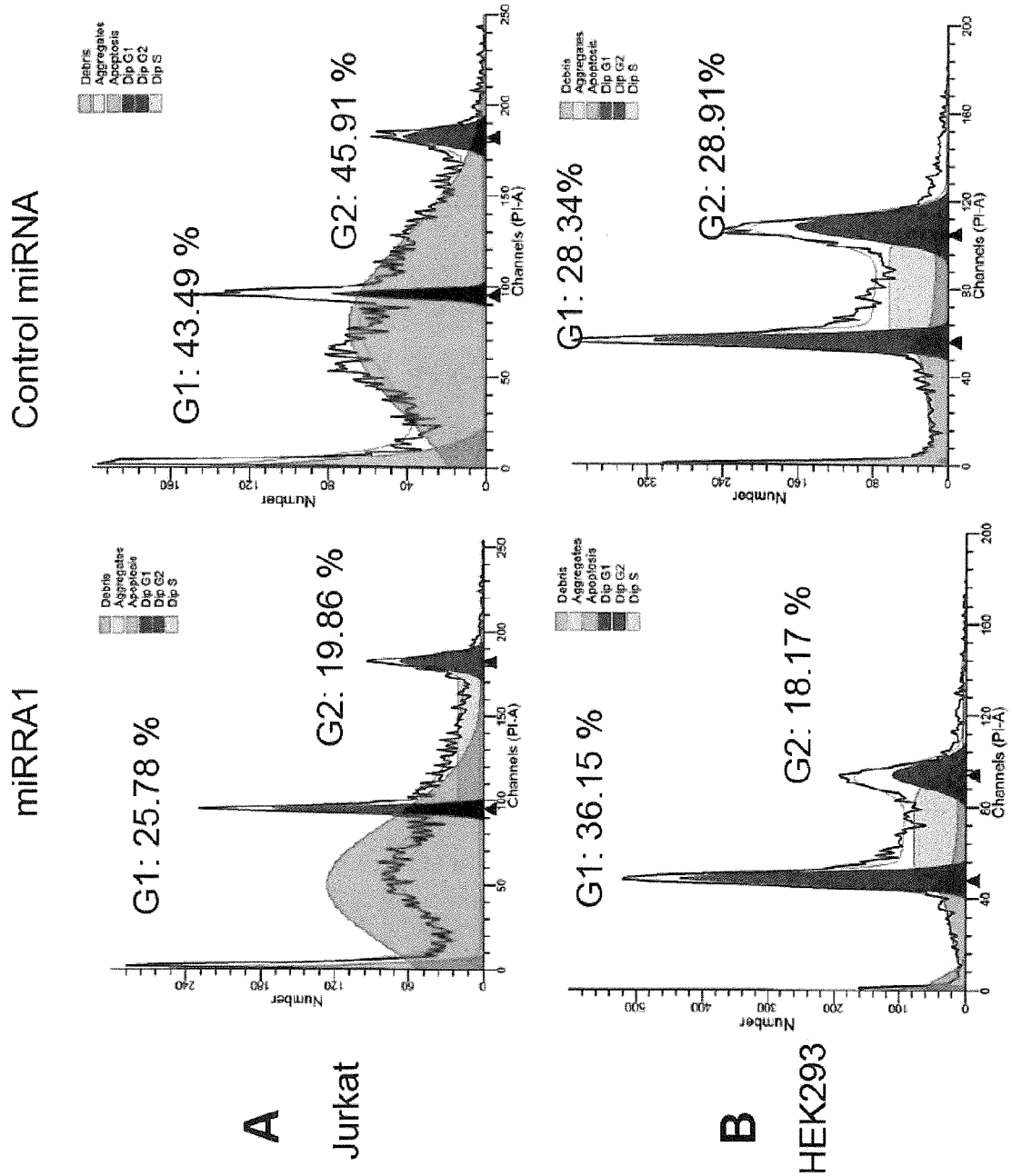
FIG. 26 shows the over-expression of miRRA1 affects cell cycle. Over-expression of miRRA1 affects the cell cycle of Jurkat cells (A) and HEK 293 cells (B) with G2 cell population decreased by about a half.
Figure 27:
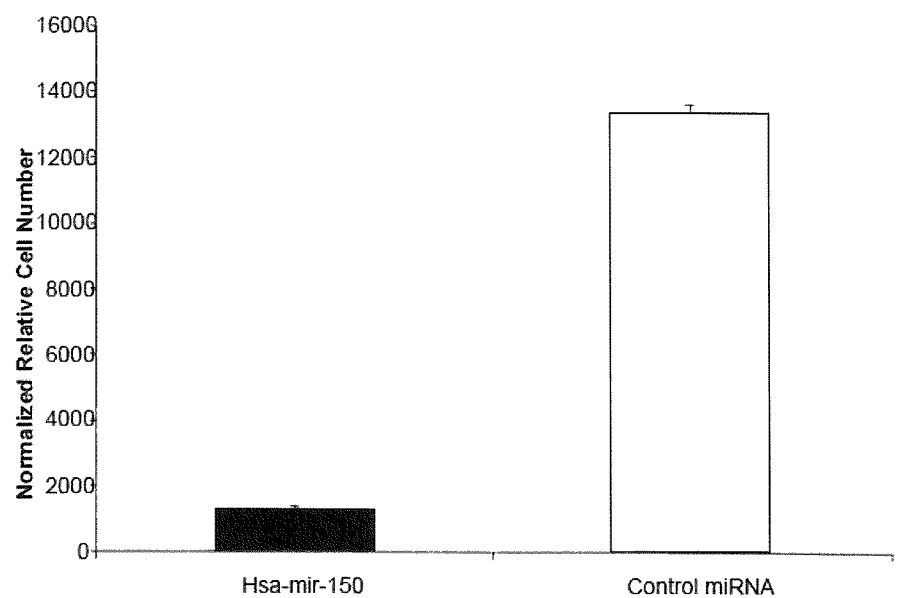
FIG. 27 shows Hsa-miRRA1 inhibits cell proliferation.
Figure 28:
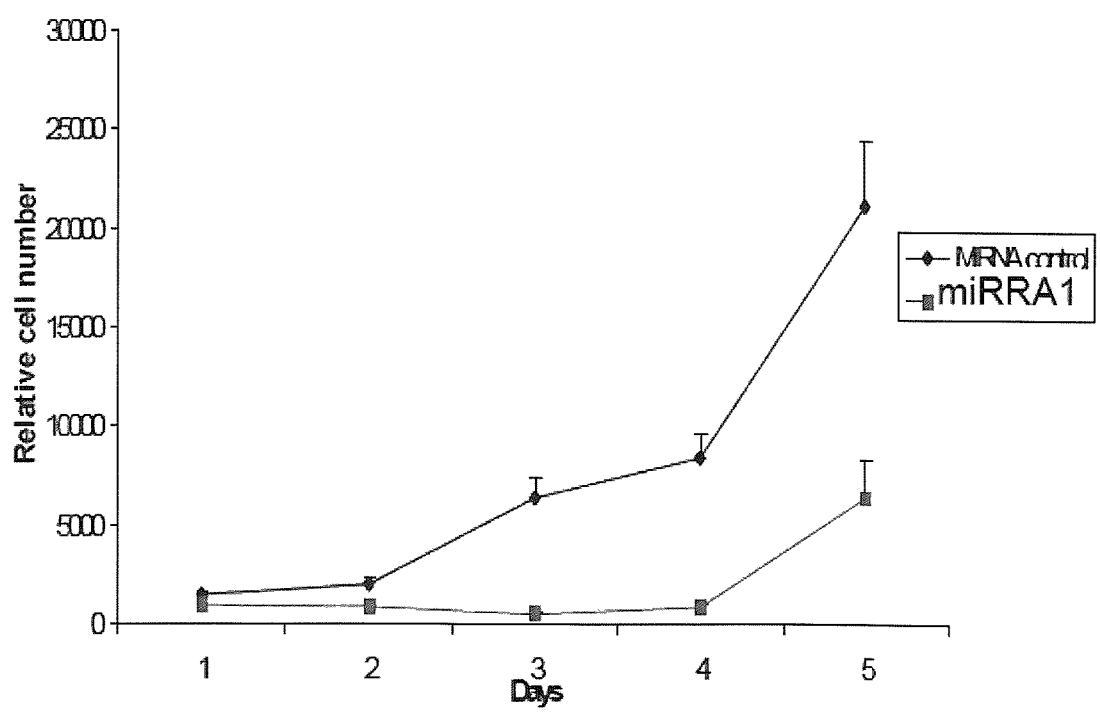
FIG. 28 shows Hsa-miRRA1 inhibits cell proliferation.
Figure 29:
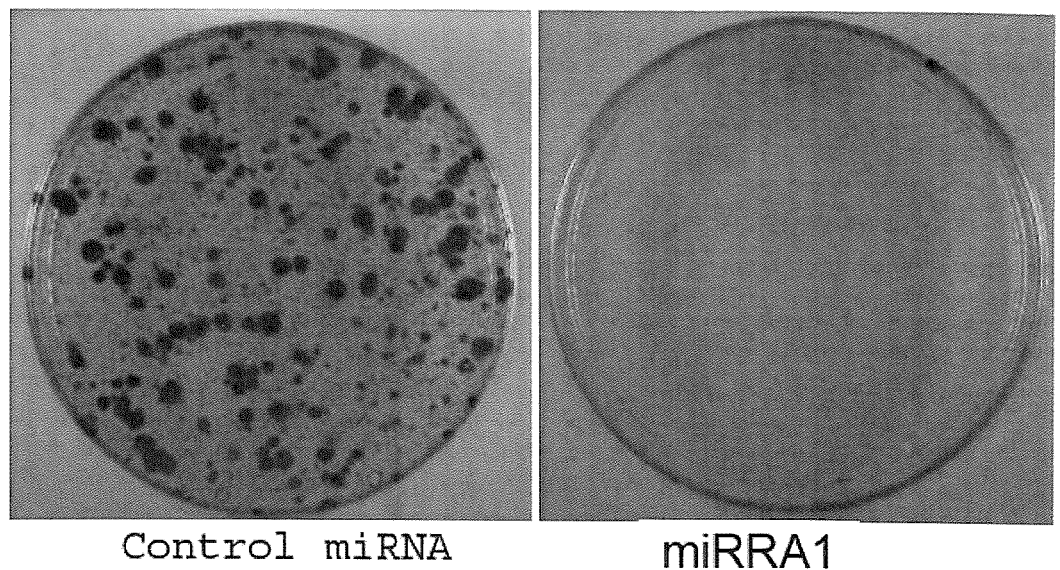
FIG. 29 shows Hsa-miRRA1 inhibits cell proliferation.
Figure 30:
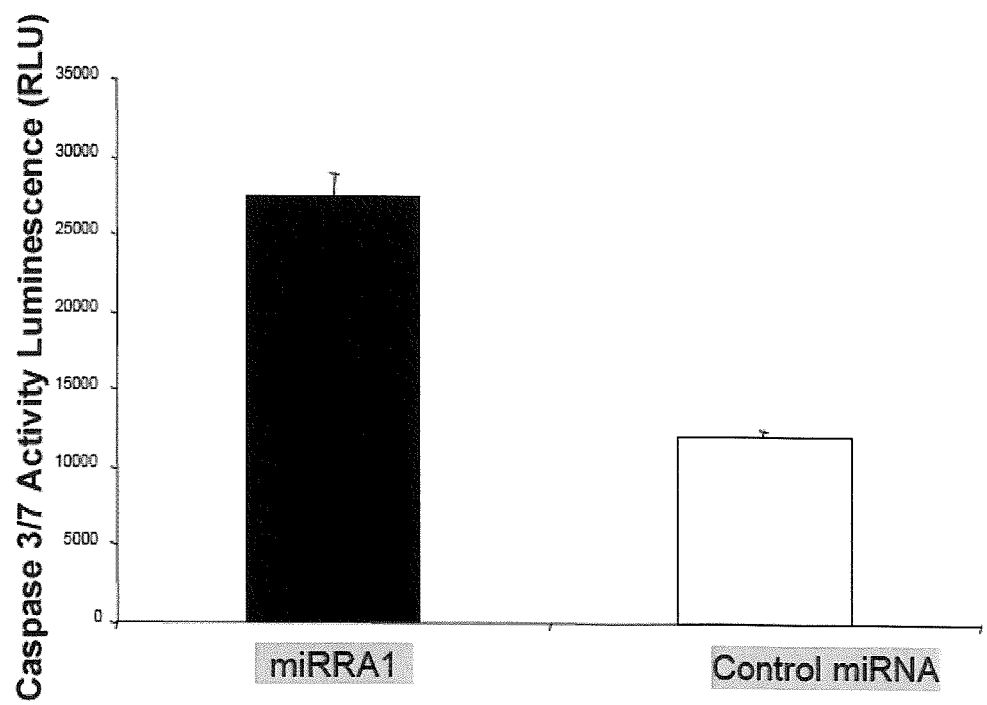
FIG. 30 shows Hsa-miRRA1 inhibits cell proliferation.

FIG. 26—Over-expression of miRRA1 affects cell cycle. Over-expression of miRRA1 affects the cell cycle of Jurkat cells (A) and HEK 293 cells (B) with G2 cell population decreased by about a half.

FIGS. 27-30—Hsa-miRRA1 inhibits cell proliferation. (FIG. 27) Cell proliferation assay of Jurkat cells infected with lentiviruses of miRRA1 or control miRNA by using the CyQUANT® NF Cell Proliferation Assay Kit. About 1,000-6,000 lentivirue-infectd cells were plated into 96-wellmicroplate wells 4 hours before assay. The fluorescence intensity of each sample was measured by using a fluorescence microplate reader (Synergy™ HT Multi-Detection Microplate Reader from Biotek) with excitation at ~485 nm and emission detection at ~530 nm. (FIG. 28) Growth cuve assay of HeLa cells stably transfected with the vectors that overexpress miRNA1 or control scramble miRNA. (FIG. 29) Colony-forming assay of A549 cells after transfected with the vectors that overexpress miRNA1 or control scramble miRNA. (FIG. 30) Hsa-miRRA1 increases caspase 3/7 activity in A549 cells induced by staurosporine. A549 cells were plated in 96-well plates and allowed to attach for 10 hours at 37° C./5% CO2. Apoptosis was induced by treating with various doses of staurosporine for 16 hours at 37° C./5% CO2. Plates were incubated at room temperature, and luminescence was recorded using a Bioteck Microplate Reader. Relative luciferase activity (RLU).

Figure 31:
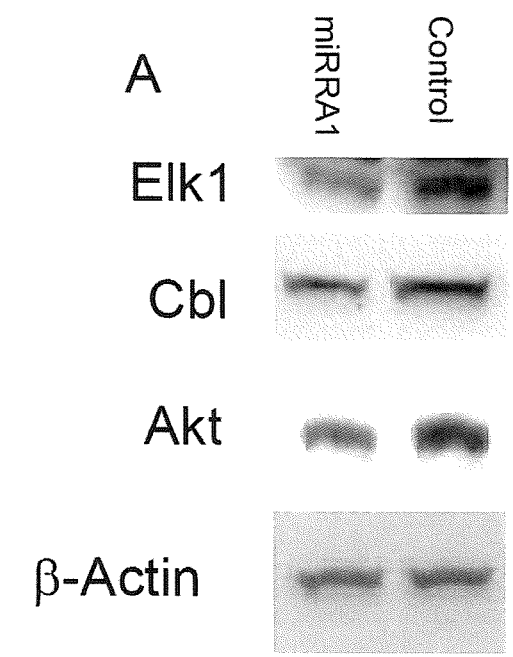
FIG. 31 shows that Hsa-miRRA1 repress the expression levels of oncogenes: Akt3 and Cbl and Elk1.
Figure 32:
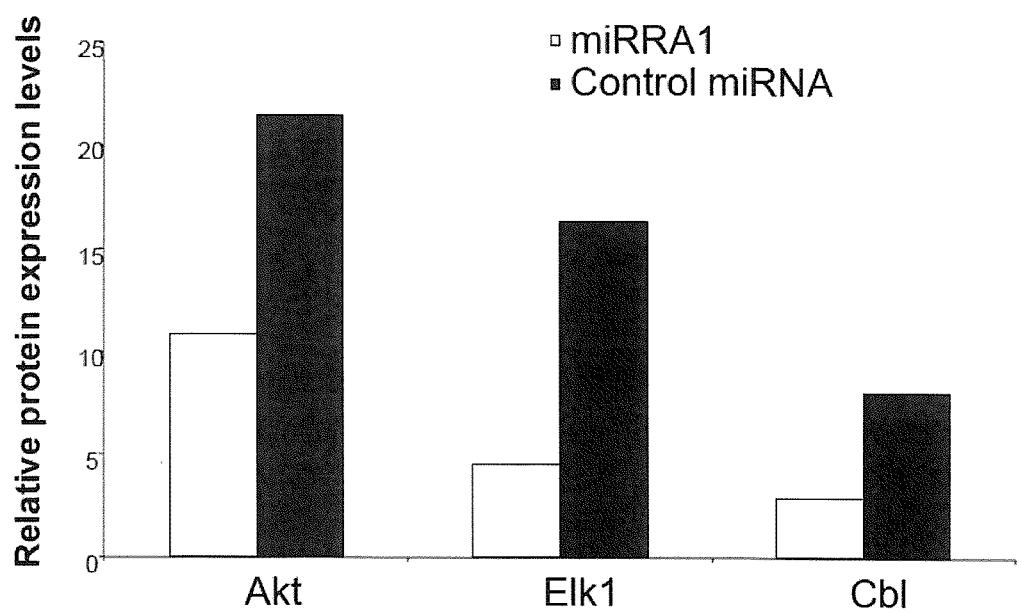
FIG. 32 shows that Hsa-miRRA1 repress the expression levels of oncogenes: Akt3 and Cbl and Elk1.

To study the underlying molecular mechanism of miRRA1 anti-inflammation properties, four bioinformatics algorithms were used to predict the most potential targets of miRRA1, some of which were further characterized by Western blot. We found that miRRA1 may directly target ELK1, CBL1 and AKT (FIGS. 31-32). These genes are involved in inflammation and cytokine production. Therefore, miRRA1 may decrease the protein levels of these genes to suppress inflammation.

FIGS. 31-32—Hsa-miRRA1 repress the expression levels of oncogenes: Akt3 and Cbl and Elk1. (FIG. 31). Western blot; (FIG. 32) Density of each band. The figures represent of three individual experiments.

Deregulation of miRNAs, especially downregulation of miRNAs, thus are involved in the pathogenesis of asthma. miRRA1 may inhibit cell proliferation through promoting apoptosis and arresting cell cycle during the pathogenesis of asthma. miRRA1 may decrease the protein levels of these genes to suppress inflammation and Th1/Th2 cytokine production.

All patent and non-patent references cited in the application, and in the corresponding provisional applications to which the present application claims priority, are hereby incorporated by reference in their entirety. The corresponding provisional applications are similarly hereby incorporated by reference in their entirety.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for treating a disease or condition associated with the downregulation of one or more miRNA in a subject, the method comprising administering to the subject an effective amount of an agent comprising a nucleic acid encoding miRRA1 in the subject and wherein the disease or condition is asthma or allergic asthma.

2. The method according to claim 1, wherein the nucleic acid is provided on a nanoparticle.

3. The method according to claim 1, wherein the method further comprises identifying that the subject has asthma or allergic asthma.

4. The method according to claim 1, wherein the agent upregulates the expression of miRRA1 in the subject.

5. The method according to claim 4, wherein the agent is a vector comprising the miRRA1 sequence.

6. The method according to claim 1, wherein the method comprises contacting a cell or cells with a nucleic acid that upregulates miRRA1 in the cell.

7. The method according to claim 1, wherein the agent is a nucleic acid provided on a nanoparticle.

8. The method according to claim 1, wherein the administering step is performed in vivo.

9. The method according to claim 1, wherein the agent is a virus.

10. The method according to claim 9, wherein the virus comprises a nucleic acid construct to express the miRRA1 in the subject.

* * * * *

UNITED STATES PATENT AND TRADEMARK OFFICE
CERTIFICATE OF CORRECTION

PATENT NO.         : 9,089,589 B2
APPLICATION NO.    : 13/772035
DATED              : July 28, 2015
INVENTOR(S)        : Shyam S. Mohapatra and Jia-Wang Wang Page 1 of 1

It is certified that error appears in the above-identified patent and that said Letters Patent is hereby corrected as shown below:

Specification

Column 13,
Line 42, "FOR amplification" should read --PCR amplification--.
Line 43, "real-time quantitative FOR" should read --real-time quantitative PCR--.

Column 23,
Line 37, "1200 uJoulex100" should read --1200uJoulex100--.

Column 26,
Line 9, "naïe" should read --naïve--.

Column 29,
Line 49, "miRRA-1.25 µg" should read --miRRA-1. 25µg--.

Signed and Sealed this
Twenty-second Day of March, 2016

Michelle K. Lee
*Director of the United States Patent and Trademark Office*

SEQUENCE LISTING

<160> NUMBER OF SEQ ID NOS: 1

<210> SEQ ID NO 1
<211> LENGTH: 22
<212> TYPE: RNA
<213> ORGANISM: Mus musculus

<400> SEQUENCE: 1
ucucccaacc cuuguaccag ug                          22